United States Patent
Happe et al.

(10) Patent No.: US 7,504,218 B2
(45) Date of Patent: Mar. 17, 2009

(54) KEY PROBE COMPOSITIONS AND METHODS FOR POLYNUCLEOTIDE DETECTION

(75) Inventors: Scott B Happe, Austin, TX (US); Joseph A Sorge, Del Mar, CA (US); Andrew Firmin, Jackson, WY (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 11/351,129

(22) Filed: Feb. 9, 2006

(65) Prior Publication Data

US 2006/0292592 A1 Dec. 28, 2006

Related U.S. Application Data

(60) Provisional application No. 60/651,310, filed on Feb. 9, 2005, provisional application No. 60/665,400, filed on Mar. 25, 2005, provisional application No. 60/688,798, filed on Jun. 9, 2005, provisional application No. 60/748,267, filed on Dec. 7, 2005.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .......... 435/6; 536/23.1, 24.3
See application file for complete search history.

(56) References Cited

U.S. PATENT DOCUMENTS

| 5,538,848 | A * | 7/1996 | Livak et al. ............ 435/6 |
| 5,925,517 | A * | 7/1999 | Tyagi et al. ............ 435/6 |
| 6,037,130 | A * | 3/2000 | Tyagi et al. ............ 435/6 |
| 6,350,580 | B1 * | 2/2002 | Sorge ................ 435/6 |
| 6,361,945 | B1 | 3/2002 | Becker |
| 6,534,274 | B2 | 3/2003 | Becker |
| 6,835,542 | B2 | 12/2004 | Becker |
| 6,849,412 | B2 | 2/2005 | Becker |
| 2006/0040275 | A1 * | 2/2006 | Rosmarin et al. ........ 435/6 |

OTHER PUBLICATIONS

Marras et al. Multiplex detection of single-nucleotide variations using molecular beacons. Genetic Analysis: Biomolecular Engineering 14 : 151-156 (1999).*

Lyamichev et al. Polymorphism identification and quantitative detection of genomic DNA by invasive cleavage of oligonucleotide probes. Nature Biotechnology 17 : 292-296 (1999).*

Ortiz et al. PNA Molecular Beacons for rapid detectiuon of PCR amplicons. Molecular and Cellular Probes 12 :219-226(1998).*

Whitcombe et al. Detection opf PCR products using self-probing amplicons and fluorescence. Nature Biotechnology 17 : 804-807 (1999).*

* cited by examiner

*Primary Examiner*—Ethan Whisenant

(57) ABSTRACT

The invention relates to compositions and methods for detection of nucleic acid sequences. The invention further relates to kit format of said compositions for detection of nucleic acid sequences. Oligonucleotide probes of the invention comprise a target binding sequence and a sequence at least partially complementary thereto, joined by an optional linker to form a hairpin structure in the absence of the target nucleic acid sequence. The probes of the invention comprise a pair of moieties that produce a detectable signal when the probe hybridizes to the target sequence.

9 Claims, 16 Drawing Sheets

Figure 10 c-kit model system

NCBI nucleotide ID (NM_000222.1, CDS)

Amplicon length = 238 bp (2674)
CCTGAACACGCCACCTGCTGAAATGTATGACATAATGAAGACTTGCTGGGATGCAGATCCC
CTAAAAAGACCAACATTCAAGCAAATTGTTCAGCTAATTGAGAAGCAGATTTCAGAGAG
CACCAATCAT*ATTACTCCAACTTAGCAAACTGCAGCCCCAACCGACAGAAGCCCGTGGTA*
GACCATTCTGTGCGGATCAATTCTGTCGGCAGCACCGCTTCCTCCTCCCAGCCTCTGC (2911)

---

Underlined medium font = forward primer (sense)
Underlined small font = reverse primer (antisense)
Bold small font = probe (antisense)
*Italics small font = upstream blocked oligo (antisense)*

Medium font = Exon 19
Large font = Exon 20
Small font = Exon 21

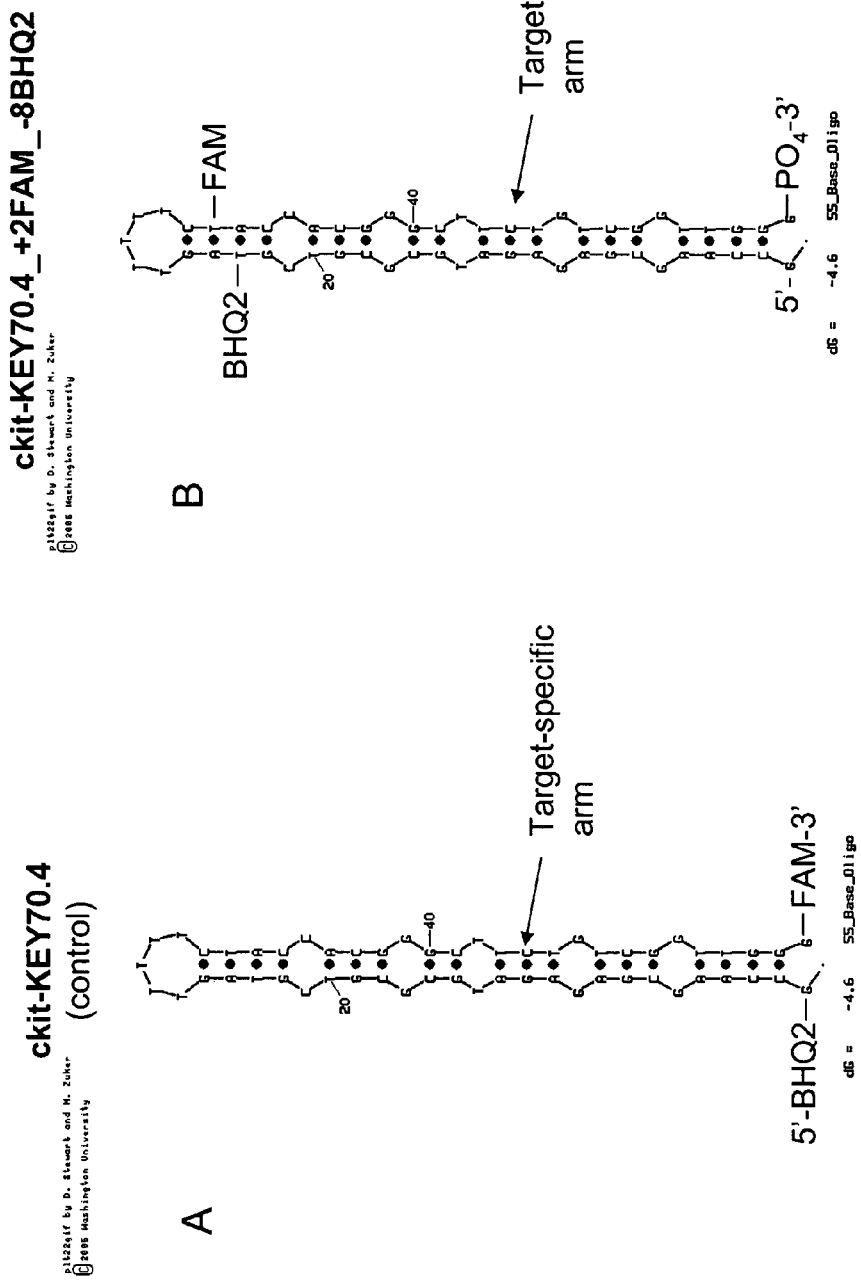
Figure 11 c-kit probes with different fluorophore/quencher positions

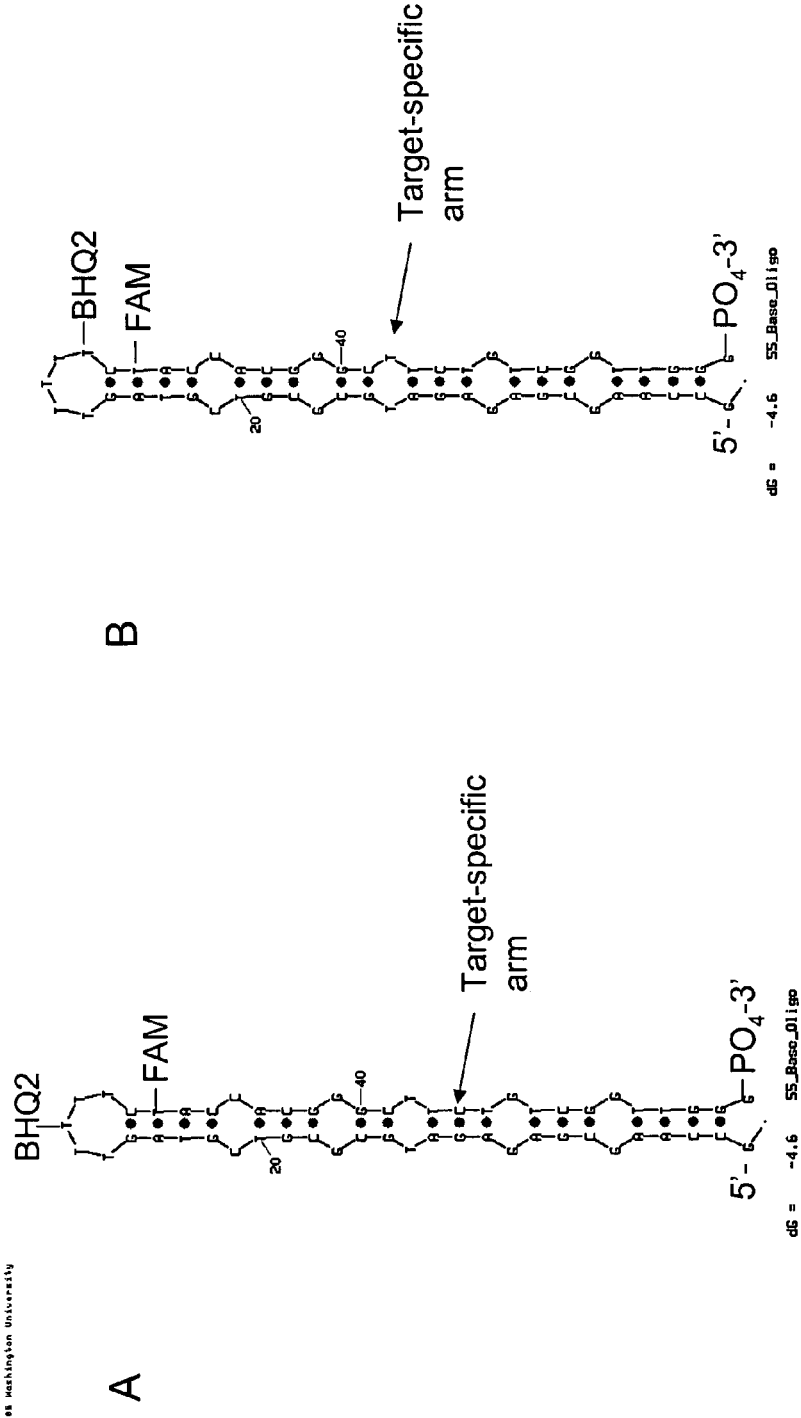
Figure 12 c-kit probes with different fluorophore/quencher positions (cont'd)

Figure 13. Upstream blocked oligos for Pfu-independent cleavage tests

5'- CCG ACA GAA TTG ATC CGC ACA GAA TGG T -3'      No nt

5'- CCG ACA GAA TTG ATC CGC ACA GAA TGG TC -3'     1 nt

5'- CCG ACA GAA TTG ATC CGC ACA GAA TGG TCT -3'    2 nt

5'- CCG ACA GAA TTG ATC CGC ACA GAA TGG TCT A -3'  3 nt

Synthetic amplicon strand
CCCAACCGACAGAAGCCCGTGGTAGACCATTCTGTGCGGATCAATTCTGTCGGPO4-3'

KEY PROBE COMPOSITIONS AND METHODS FOR POLYNUCLEOTIDE DETECTION

This application claims the benefit of U.S. Provisional Application Nos. 60/651,310, filed on Feb. 9, 2005, 60/665,400, filed on Mar. 25, 2005, 60/688,798, filed on Jun. 9, 2005, and 60/748,267, filed on Dec. 7, 2005 each of which is incorporated herein by reference in its entirety.

TECHNICAL FIELD

The invention relates to probes for the detection of nucleic acid sequences.

BACKGROUND

Techniques for polynucleotide detection have found widespread use in basic research, diagnostics, and forensics. Polynucleotide detection can be accomplished by a number of methods. Most methods rely on the use of the polymerase chain reaction (PCR) to amplify the amount of target DNA.

The TaqMan™ assay is a homogenous assay for detecting polynucleotides (see U.S. Pat. No. 5,723,591). In this assay, two PCR primers flank a central probe oligonucleotide. The probe oligonucleotide contains a fluorophore and quencher. During the polymerization step of the PCR process, the 5' nuclease activity of the polymerase cleaves the probe oligonucleotide, causing the fluorophore moiety to become physically separated from the quencher, which increases fluorescence emission. As more PCR product is created, the intensity of emission at the novel wavelength increases. However, background emission can be rather high with this method, due to the required separation of the fluorophore and quencher in the probe oligonucleotide.

Molecular beacons are an alternative to TaqMan for the detection of polynucleotides (see U.S. Pat. Nos. 6,277,607; 6,150,097; and 6,037,130). Molecular beacons are oligonucleotide hairpins which undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thus increasing the signal derived from the fluorophore.

The adjacent probes method amplifies the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair. Upon hybridization of the two probes with the target sequence, the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target amount. U.S. Pat. No. 6,174,670B1 discloses such methods.

Sunrise primers utilize a hairpin structure similar to molecular beacons, but attached to a target binding sequence which serves as a primer. When the primer's complementary strand is synthesized, the hairpin structure is disrupted, thereby eliminating quenching. These primers detect amplified product and do not require the use of a polymerase with a 5' exonuclease activity. Sunrise primers are described by Nazarenko et al. (Nucleic Acids Res. 25:2516-21 (1997) and in U.S. Pat. No. 5,866,336.

Scorpion probes combine a primer with an added hairpin structure, similar to Sunrise primers. However, the hairpin structure of Scorpion probes is not opened by synthesis of the complementary strand, but by hybridization of part of the hairpin structure with a portion of the target which is downstream from the portion which hybridizes to the primer.

DzyNA-PCR involves a primer containing the antisense sequence of a DNAzyme, an oligonucleotide capable of cleaving specific RNA phosphodiester bonds. The primer binds to a target sequence and drives an amplification reaction producing an amplicon which contains the active DNAzyme. The active DNAzyme then cleaves a generic reporter substrate in the reaction mixture. The reporter substrate contains a fluorophore-quencher pair, and cleavage of the substrate produces a fluorescence signal which increases with the amplification of the target sequence. Dzy-PCR is described in Todd et al., Clin. Chem. 46:625-30 (2000), and in U.S. Pat. No. 6,140,055.

There is a need in the art for novel probes and methods to detect nucleic acid sequences and monitor amplification reactions, particularly in real time. There is also a need to improve the sensitivity, signal-to-noise ratio, specificity, allelic discrimination, and ease of design of such probes and detection methods.

SUMMARY OF THE INVENTION

The invention is related to novel compositions and methods for nucleic acid detection.

The invention provides an oligonucleotide probe for detecting a target nucleic acid sequence. The probe comprises a first sequence which is at least partially complementary to a target sequence and a second sequence which is at least partially complementary to the first sequence. The probe further comprises a first moiety operatively coupled to the first sequence and a second moiety operatively coupled to the second sequence. The 3' end of the first sequence is linked to the 5' end of the second sequence; alternatively the 5' end of the first sequence is linked to the 3' end of the second sequence. The first sequence and the second sequence are capable of hybridizing to each other when the probe is not hybridized to the target sequence. Hybridization of the probe to the target sequence causes either the first moiety or the second moiety to produce a detectable signal. In some embodiments, hybridization of the probe to the target sequence causes the formation of either a 3' flap or a 5' flap. Probes having the first sequence at the 5' end of the probe may form a 3' flap when bound to a target nucleic acid, and probes having the first sequence at the 3' end of the probe may form a 5' flap when bound to a target nucleic acid.

In a preferred embodiment, the probe further comprises a linker sequence covalently joined to the first sequence and the second sequence. The linker sequence is not completely complementary to the target sequence, the first sequence, or the second sequence, although some nucleotides of the linker may hybridize to those regions. However, in other embodiments the 3' end of the first sequence is directly linked to the 5' end of the second sequence, or the 5' end of the first sequence is directly linked to the 3' end of the second sequence, without the use of a linker sequence. If present, the linker sequence is from about 1 to about 100 nucleotides in length, or from about 4 to about 10 nucleotides in length, or about 5 nucleotides in length. No more than 5 contiguous nucleotides of the optional linker sequence are complementary to the target sequence. In certain embodiments, no more than 4, 3, or 2 contiguous nucleotides of the linker are complementary to the target sequence. In some embodiments comprising a linker, no more than 5, 4, 3, or 2 nucleotides anywhere in the linker are complementary to the target sequence when the target sequence is aligned for optimum complementarity to the first sequence.

The probes of the invention produce a detectable signal, such as an increase in fluorescence emission, upon binding to the target sequence. The detectable signal is produced when the first and second moieties become physically separated upon hybridization of the target binding sequence (first sequence) to the target. The first and second moieties are operationally coupled to the first and second sequences, respectively. The first and second moieties may be coupled at or near the opposite ends of the probe, which come into close proximity when the probe forms a stem or hairpin structure. Preferably the first and second moieties are covalently attached to the probe. In some embodiments the moieties are attached at or near the 5' and 3' ends of the probe. In certain embodiments, one of the moieties is attached at the 3' end of the probe, thereby preventing elongation of the probe by a polymerase. In preferred embodiments, the first and second moieties are a fluorophore/quencher pair positioned on the probe so as to result in quenching when the probe is not bound to the target sequence (i.e., in the stem or hairpin configuration), but lack of quenching (i.e., fluorescence) when the probe hybridizes with the target. In certain embodiments a set of probes designed to recognize nucleotide polymorphisms in a nucleic acid sequence can have different moieties for each possible nucleotide polymorphism, each providing a distinct signal which allows simultaneous detection or quantification of two or more target sequences.

The target binding sequence (first sequence) of the probe is at least 5 nucleotides in length. In preferred embodiments, the target binding sequence is about 15 to about 60 nucleotides in length. In more preferred embodiments, the target binding sequence is about 15 to about 30 nucleotides in length. In certain embodiments, the target binding sequence is about 10 to about 15 nucleotides in length and optionally includes at least one modified nucleotide that increases the $T_m$ of the probe when hybridized to the target.

The second sequence of the probe is at least partially complementary to the first sequence and is capable of hybridizing to the first sequence when the first sequence is not hybridized to the target sequence. For example, the second sequence may form the stem portion of a hairpin structure when the probe is not bound to the target sequence. The second sequence is at least 5 nucleotides in length. Preferably, the second sequence is similar in length to the first sequence. The second sequence can be fully complementary to the first sequence. However, in preferred embodiments, there is at least one mismatch between the first sequence and the second sequence. Preferably, there are from about 2 to about 8 mismatches between the first and second sequences, or from about 3 to about 6 mismatches. In certain embodiments, the number of mismatches between the first and second sequences corresponds to from about 10% to about 30% of the length of the first sequence.

In preferred embodiments, the $T_m$ of the stem structure formed by the first and second sequences in the absence of target sequence is approximately equal to the annealing temperature of the PCR cycle or hybridization assay, or up to 5-20 degrees C. higher than the annealing temperature. Probes with $T_m$ more than 20 degrees C. higher than the annealing temperature will have difficulty unfolding, or will be unable to unfold during a PCR or hybridization analysis. The $T_m$ of a probe is influenced by the length of the stem portion of the probe and number of mismatches in the stem portion of the probe. In general, each additional mismatch added to the stem region will further reduce $T_m$. Therefore, the number of mismatches can be adjusted to give a desired $T_m$. Mismatches can be positioned at any location within the stem portion of the probe, at either end or in the middle, either grouped or separated. Furthermore, $T_m$ can be modified through the introduction of modified nucleotides, including for example minor groove binders and locked nucleic acids (LNA). Introduction of such modified nucleotides can be used to increase the affinity for the target sequence, to reduce the length of the target binding sequence, or to reduce the number of mismatches required for a desired $T_m$.

The invention also provides compositions comprising a probe for detecting a target nucleic acid sequence. The probe comprises a first sequence which is at least partially complementary to a target sequence and a second sequence which is at least partially complementary to the first sequence. The probe further comprises a first moiety operationally coupled to the first sequence and a second moiety operationally coupled to the second sequence. The 3' end of the first sequence is linked to the 5' end of the second sequence, or the 5' end of the first sequence is linked to the 3' end of the second sequence. The first sequence and the second sequence are capable of hybridizing to each other, for example, forming a stem or hairpin structure when the probe is not hybridized to the target sequence. Hybridization of the probe to the target sequence causes either the first moiety or the second moiety to produce a detectable signal. In some embodiments the composition comprises the probe and one or more primers for amplification of the target nucleic acid sequence. In certain embodiments the composition comprises a plurality of probes and a plurality of primers or primer pairs, which can be used, for example, to perform multiplex PCR, in which a plurality of target sequences are detected and amplified simultaneously. In other embodiments the composition comprises the probe and a nucleic acid polymerase. In still other embodiments, the composition comprises the probe, one or more primers for amplification of the target sequence, and a nucleic acid polymerase. In yet other embodiments, the composition comprises a plurality of probes, a plurality of primers or primer pairs for amplification of the target sequences detected by the plurality of probes, and a nucleic acid polymerase. In other embodiments, the composition comprises the probe and a cleavage agent, such as a nuclease. Still other embodiments of the composition include the probe, a cleavage agent, and one or more nucleic acid polymerases.

In certain embodiments, the oligonucleotide probe of the invention comprises a first moiety and a second moiety which serve as an interactive pair of labels comprising a fluorophore and a quencher or a FRET pair. The fluorophore or quencher can be attached to a 3' nucleotide of the probe and the other of the fluorophore/quencher pair can be attached to a 5' nucleotide of the probe. The interactive pair of labels may be separated by 10, 20, 30, 40, 50, 60 or more nucleotides, yet they are brought into closer proximity in the hairpin configuration. The fluorophore can be, for example, a FAM, R110, TAMRA, R6G, CAL Fluor Red 610, CAL Fluor Gold 540, or CAL Fluor Orange 560 and the quencher can be, for example, a DABCYL, BHQ-1, BHQ-2, or BHQ-3. In some embodiments, the detectable signal increases upon hybridization to the target sequence by at least 2 fold.

The oligonucleotide probe can be used for detecting a target nucleic acid in a sample by contacting the sample with the oligonucleotide probe and determining the presence of the target nucleic acid in the sample. A change in the intensity of the signal is indicative of the presence of the target nucleic acid.

One embodiment of the invention provides for a further method of detecting a target nucleic acid in a sample by providing a PCR mixture which includes the oligonucleotide probe, a nucleic acid polymerase, and a pair of primers. The PCR mixture is contacted with the sample to produce a PCR sample mixture and the PCR sample mixture is incubated to allow amplification of the target nucleic acid. The generation of a detectable signal is indicative of the presence of the target nucleic acid in the sample.

In additional aspects of the invention, the probes are part of a kit for generating a signal indicative of the presence of a target nucleic acid sequence in a sample. The kit may include the probe, a nucleic acid polymerase, a PCR buffer, one or more primers, and packaging material therefor.

The invention also provides a method of detecting a target nucleic acid sequence in a sample. The method comprising the steps of (1) incubating a sample suspected of containing the target sequence with a probe capable of binding to a target nucleic acid sequence and (2) determining whether a detectable signal is produced which is characteristic of the probe binding to the target sequence, in which case the target sequence is detected in the sample. The probe comprises (a) a first sequence which is at least partially complementary to a target sequence; (b) a second sequence which is at least partially complementary to the first sequence; (c) a first moiety operationally coupled to said first sequence; and (d) a second moiety operationally coupled to said second sequence. The 3' end of the first sequence is linked to the 5' end of the second sequence; alternatively the 5' end of the first sequence is linked to the 3' end of the second sequence. The first sequence and the second sequence are capable of hybridizing to each other and may form a stem structure when the probe is not hybridized to the target sequence. Hybridization of the probe to the target sequence causes either the first moiety or the second moiety to produce a detectable signal. In some embodiments of this method, the steps of incubating and determining are performed while concurrently amplifying a nucleic acid comprising the target sequence from the sample using an amplification method such as polymerase chain reaction, e.g. by performing "real time" PCR.

The invention further provides a method of quantifying a target sequence in a sample. The method comprises the steps of (1) detecting a target nucleic acid sequence in a sample by the method described in the preceding paragraph and (2) comparing the signal to a standard curve to obtain the quantity of the target sequence in the sample. In some embodiments of this method, the step of detecting is performed while concurrently amplifying a nucleic acid comprising the target sequence from the sample using an amplification method such as polymerase chain reaction, e.g. by performing "real time" PCR.

The invention also provides a method of discriminating between a first and a second nucleic acid target sequence in a sample, when the target sequences differ by one or more nucleotides at a polymorphic site. The method comprises the steps of (1) detecting the first target nucleic acid sequence in a sample by the method described above using a first probe having a target binding sequence which is fully complementary to the first target sequence; (2) detecting the second target nucleic acid sequence in a sample by the method described above using a second oligonucleotide probe having a target binding sequence which is fully complementary to the second target sequence; and (3) measuring whether said first probe or said second probe produces a detectable signal, thereby detecting the presence of either the first or second target sequence, or a mixture of both. In some embodiments, this method can be employed quantitatively to determine the amounts of different forms of a sequence (e.g., two or more alleles, wild type and mutation, etc.) are present in a sample. For example, the signals of the first probe and the second probe can be compared to a standard curve to obtain the quantities of the first and second target sequence in the sample.

A variation of the above method of determining whether a first or a second nucleic acid target sequence is present in a sample utilizes first and second probes which produce distinguishable signals upon hybridization to their respective target sequences. For example, the probes can employ two different fluorophores, each with a characteristic emission wavelength. In this way, two or more variants at a polymorphic locus can be detected or quantified simultaneously.

Further features and advantages of the invention and further embodiments will become more fully apparent in the following description of the embodiments and drawings thereof, and from the claims.

BRIEF DESCRIPTION OF DRAWINGS

FIG. 5 depicts the results of an allelic discrimination assay using (FIG. 5A) the wild-type eNOS-specific Key Probe of FIG. 4A and (FIG. 5B) the mutant eNOS-specific Key Probe of FIG. 4B.

FIG. 6 demonstrates the template specificity of allele-specific eNOS Key Probes. Reactions were performed using both wild-type specific and mutant-specific eNOS Key Probes in the presence of various mixtures of wild-type and mutant templates, as indicated.

FIG. 10 shows an exemplary target amplicon used to test various Key probes for their ability to generate a signal indicative of the presence of the target.

FIG. 11 shows examples of a control Key probe (FIG. 11A) and a test Key probe (FIG. 11B).

FIGS. 12A and B show examples of Key probes.

FIG. 13 shows examples of upstream 3' blocked probes having between 0 and 3 residues of overlap with the 5' end of the complementary region of the downstream Key probe.

DETAILED DESCRIPTION OF THE INVENTION

Definitions

Figure 1:
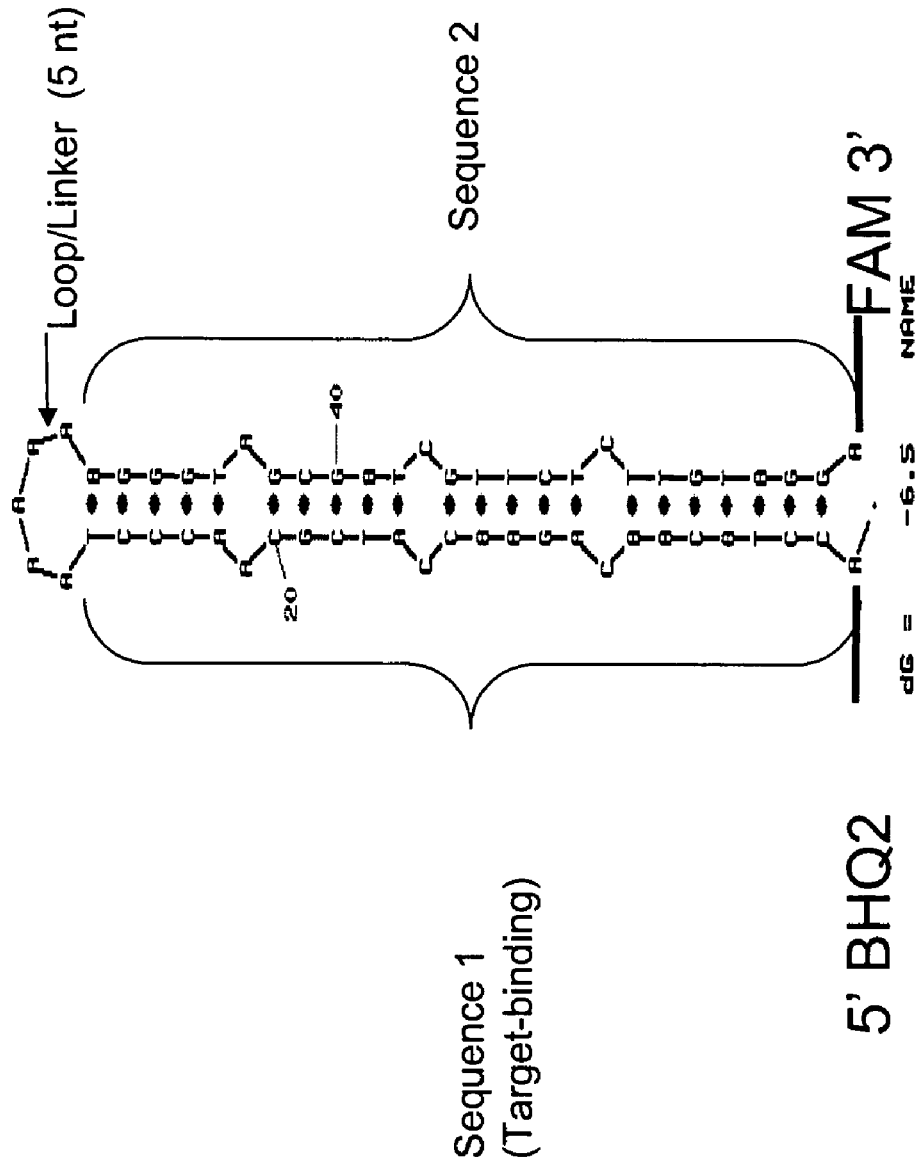
FIG. 1 illustrates the sequence and secondary structure of a Key Probe specific for a Group B Streptococcus sequence.

As used herein, a "polynucleotide" refers to a covalently linked sequence of nucleotides (i.e., ribonucleotides for RNA and deoxyribonucleotides for DNA) in which the 3' position of the pentose of one nucleotide is joined by a phosphodiester linkage to the 5' position of the pentose of the next nucleotide. The term "polynucleotide" includes single- and double-stranded polynucleotides. The term "polynucleotide" as it is employed herein embraces chemically, enzymatically, or metabolically modified forms of polynucleotide. "Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur between the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A "terminal nucleotide", as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'-ends.

Polynucleotides according to the invention may contain modified polynucleotides including locked nucleic acids (LNA), peptide nucleic acids (PNA), and the like. A PNA is a polyamide type of DNA analog, and the monomeric units for adenine, guanine, thymine and cytosine are available commercially (Applied Biosystems, Inc., Foster City, Calif.). Certain components of DNA, such as phosphorus, phosphorus oxides, or deoxyribose derivatives, are not present in PNAs. As disclosed by Nielsen et al., Science 254, 1497 (1991) and Egholm et al., Nature 365, 666 (1993), PNAs bind specifically and tightly to complementary DNA strands and are not degraded by nucleases. PNA/DNA duplexes bind under a wider range of stringency conditions than DNA/DNA duplexes, making it easier to perform multiplex hybridization. Smaller probes can be used than with DNA due to the strong binding. A single mismatch in a PNA/DNA 15-mer lowers the melting point ($T_m$) by 8-20 degrees C. vs. 4-16 degrees C. for the corresponding DNA/DNA 15-mer duplex. The absence of charged groups in PNA permits hybridization to be done at low ionic strengths. The synthesis and properties of LNAs are described in Koshkin et al., Tetrahedron, 54, 3607-3630 (1998) as well as in Wengel U.S. Pat. No. 6,794, 499. LNA-containing oligonucleotides can be obtained commercially, for example from Proligo, LLP (Boulder, Colo.).

Furthermore, polynucleotides of the invention may comprise one or more modified bases selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 8-azaguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, and 2,6-diaminopurine.

As used herein, the term "oligonucleotide" refers to a short polynucleotide, typically less than or equal to 150 nucleotides long (e.g., between 5 and 150, preferably between 10 and 100, more preferably between 15 and 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

As used herein, the term "complementary" refers to the concept of sequence complementarity between regions of two polynucleotide strands or between two regions of the same polynucleotide strand. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" can refer to one polynucleotide that is 100% or "fully" complementary to another polynucleotide and thus forms a base pair at every nucleotide position. "Complementary" also can refer to one polynucleotide that is not 100% complementary (e.g., that is 90%, 80%, 70% complementary or less) to another polynucleotide which contains mismatched nucleotides at one or more nucleotide positions. As used herein, "at least partially complementary" means that less than 100%, (e.g., 99%, 90%, 75%, 50%, 25% etc . . . ) of the nucleotides of one polynucleotide can form base pairs with nucleotides of another polynucleotide. Where an oligonucleotide is "partially complementary," the region of complementary nucleotides may or may not be contiguous nucleotides.

As used herein, the term "hybridization" or "binding" is used to describe the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved, the melting temperature ($T_m$) of the formed hybrid, the presence of other components (e.g., the presence or absence of polyethylene glycol), the molarity of the hybridizing strands, and the G:C content of the polynucleotide strands.

As used herein, when one polynucleotide is said to "hybridize" to another polynucleotide, it means that there is some complementarity between the two polynucleotides or that the two polynucleotides form a hybrid under high stringency conditions. When one polynucleotide is said to not hybridize to another polynucleotide, it means that there is essentially no sequence complementarity between the two polynucleotides or that no hybrid forms between the two polynucleotides at a high stringency condition. In one embodiment, two complementary polynucleotides are capable of hybridizing to each other under high stringency hybridization conditions. Hybridization under stringent conditions is typically established by performing membrane hybridization (e.g., Northern hybridization) under high stringency hybridization conditions, defined as incubation with a radiolabeled probe in 5×SSC, 5× Denhardt's solution, 1% SDS at 65° C. Stringent washes for membrane hybridization are performed as follows: the membrane is washed at room temperature in 2×SSC/0.1% SDS and at 65° C. in 0.2×SSC/0.1% SDS, 10 minutes per wash, and exposed to film.

As used herein, a "primer" refers to a type of oligonucleotide having or containing the length limits of an "oligonucleotide" as defined above, and having or containing a sequence complementary to a target polynucleotide, which hybridizes to the target polynucleotide through base pairing so to initiate an elongation (extension) reaction to incorporate a nucleotide into the oligonucleotide primer. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer is preferably single-stranded for maximum efficiency in amplification. "Primers" useful in the present invention are generally between about 10 and 1000 nucleotides in length, preferably between about 14 and 50 nucleotides in length, and most preferably between about 17 and 45 nucleotides in length. An "amplification primer" is a primer for amplification of a target sequence by primer extension. As no special sequences or structures are required to drive the amplification reaction, amplification primers for PCR may consist only of target binding sequences. A "primer region" is a region on an "oligonucleotide probe" or a "bridging oligonucleotide probe" which hybridizes to the target nucleic acid through base pairing so to initiate an elongation reaction to incorporate a nucleotide into the oligonucleotide primer.

As used herein, a polynucleotide "isolated" from a sample is a naturally occurring polynucleotide sequence within that sample which has been removed from its normal cellular environment. Thus, an "isolated" polynucleotide may be in a cell-free solution or placed in a different cellular environment.

As used herein, the term "amount" refers to an amount of a target polynucleotide in a sample, e.g., measured in μg, μmol or copy number. The abundance of a polynucleotide in the present invention is measured by the fluorescence intensity emitted by such polynucleotide, and compared with the fluorescence intensity emitted by a reference polynucleotide, i.e., a polynucleotide with a known amount.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. A "probe which shares no homology with another polynucleotide" refers to a probe whose homology to the polynucleotide, as measured by BLASTN version 2.0 using the default parameters, is no more than 55%, e.g., less than 50%, or less than 45%, or less than 40%, or less than 35%, in a contiguous region of 20 nucleotides or more.

A "hairpin structure", as used herein, comprises two self-complementary sequences that may form a double-stranded "stem" region, optionally separated at one end by a loop sequence. The two regions of the oligonucleotide which comprise the double-stranded stem region are substantially complementary to each other, resulting in self-hybridization. However, the stem can include one or more mismatches, insertions or deletions. The "hairpin structure", as used herein, can additionally comprise single-stranded region(s) that extend from the double-stranded stem segment.

As used herein, "$T_m$," and "melting temperature" are interchangeable terms which are the temperature at which 50% of a population of double-stranded polynucleotide molecules becomes dissociated into single strands. Equations for calculating the $T_m$ of polynucleotides are well known in the art. For example, the $T_m$ may be calculated by the following equation: $T_m = 69.3 + 0.41 \times (G+C)\% - 650/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×4° C.], see, for example, C. R. Newton et al. PCR, $2^{nd}$ Ed., Springer-Verlag (New York: 1997), p. 24. Other more sophisticated computations exist in the art, which take structural as well as sequence characteristics into account for the calculation of $T_m$. A calculated $T_m$ is merely an estimate which can be used to predict an appropriate temperature for a given hybridization or dissociation step; the optimum temperature is commonly determined empirically.

A "nucleotide analog", as used herein, refers to a nucleotide in which the pentose sugar and/or one or more of the phosphate esters are replaced with their respective analogs. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. A nucleotide analog can also be an LNA or a PNA (see above).

As used herein, the term "sample" refers to a biological material which is isolated from its natural environment and contains a polynucleotide. A "sample" according to the invention may consist of purified or isolated polynucleotide, or it may comprise a biological sample such as a tissue sample, a biological fluid sample, or a cell sample comprising a polynucleotide. A biological fluid can be, for example, blood, plasma, sputum, urine, cerebrospinal fluid, lavages, and leukophoresis samples. A sample of the present invention may be a plant, animal, bacterial or viral material containing a target polynucleotide. Useful samples of the present invention may be obtained from different sources, including, for example, but not limited to, from different individuals, different developmental stages of the same or different individuals, different diseased individuals, normal individuals, different disease stages of the same or different individuals, individuals subjected to different disease treatments, individuals subjected to different environmental factors, individuals with predisposition to a pathology, individuals with exposure to an infectious disease (e.g., HIV). Useful samples may also be obtained from in vitro cultured tissues, cells, or other polynucleotide containing sources. The cultured samples may be taken from sources including, but are not limited to, cultures (e.g., tissue or cells) cultured in different media and conditions (e.g., pH, pressure, or temperature), cultures (e.g., tissue or cells) cultured for different period of length, cultures (e.g., tissue or cells) treated with different factors or reagents (e.g., a drug candidate, or a modulator), or cultures of different types of tissue or cells.

As used herein, "nucleic acid polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19:4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzyme can be determined by means well known in the art. One unit of DNA polymerase activity, according to the subject invention, is defined as the amount of enzyme which catalyzes the incorporation of 10 nmoles of total dNTPs into polymeric form in 30 minutes at optimal temperature (e.g., 72° C. for Pfu DNA polymerase).

"Primer extension reaction" or "synthesizing a primer extension" means a reaction between a target-primer hybrid and a nucleotide which results in the addition of the nucleotide to a 3'-end of the primer such that the incorporated nucleotide is complementary to the corresponding nucleotide of the target polynucleotide. Primer extension reagents typically include (i) a polymerase enzyme, (ii) a buffer, and (iii) one or more extendible nucleotides.

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxyribonucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule. The PCR process is described in U.S. Pat. Nos. 4,683,195 and 4,683,202, the disclosures of which are incorporated herein by reference.

As used herein a "nuclease" or a "cleavage agent" refers to an enzyme that is specific for, that is, cleaves a "cleavage structure" according to the invention and is not specific for, that is, does not substantially cleave either a probe or a primer that is not hybridized to a target nucleic acid, or a target nucleic acid that is not hybridized to a probe or a primer. The term "nuclease" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), *Pyrococcus furiosus* (Pfu) and *Thermus flavus* (Tfl). The term "nuclease" also embodies FEN nucleases.

As used herein a "flap" refers to a region of single stranded DNA that extends from a double stranded nucleic acid molecule. The length of a flap according to the invention is preferably in the range from about 1 to about 500 nucleotides, more preferably from about 5 to about 25 nucleotides, and most preferably from about 10 to about 20 nucleotides.

As used herein, a "cleavage structure" refers to a polynucleotide structure comprising at least a duplex nucleic acid having a single stranded region comprising a flap, a loop, a single-stranded bubble, a D-loop, a nick or a gap. A cleavage structure according to the invention thus includes a polynucleotide structure comprising a flap strand of a branched DNA wherein a 5' single-stranded polynucleotide flap extends from a position near its junction to the double stranded portion of the structure, and preferably the flap is labeled with a detectable label. A flap of a cleavage structure according to the invention is preferably cleaved at a position located either one nucleotide proximal to and/or one nucleotide distal from the elbow of the flap strand. In some embodiments, a flap of a cleavage structure does not hybridize to a target nucleic acid sequence.

A cleavage structure according to one embodiment of the invention preferably comprises a target nucleic acid sequence, and also may include an oligonucleotide probe according to the invention, hybridized with the target nucleic acid sequence via a region or regions that are at least partially complementary to the target nucleic acid, and a flap extending from the hybridizing oligonucleotide probe.

FEN-1 is an approximately 40 kDa, divalent metal ion-dependent exo- and endonuclease that specifically recognizes the backbone of a 5' single-stranded flap strand and tracks down this arm to the cleavage site, which is located at the junction wherein the two strands of duplex DNA adjoin the single-stranded arm. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer).

This is also the case for *E. coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

fen-1 genes encoding FEN-1 enzymes useful in the invention include murine fen-1, human fen-1, rat fen-1, *Xenopus laevis* fen-1, and fen-1 genes derived from four archaebacteria *Archaeglobus fulgidus, Methanococcus jannaschii, Pyrococcus furiosus* and *Pyrococcus horikoshii*. CDNA clones encoding FEN-1 enzymes have been isolated from human (GenBank Accession Nos. NM.sub.—004111 and L37374), mouse (GenBank Accession No. L26320), rat (GenBank Accession No.: AA819793), *Xenopus laevis* (GenBank Accession Nos. U68141 and U64563), and *P. furiosus* (GenBank Accession No. AF013497). The complete nucleotide sequence for *P. horikoshii* flap endonuclease has also been determined (GenBank Accession No. AB005215). The FEN-1 family also includes the *Saccharomyces cerevisiae* RAD27 gene (GenBank Accession No. Z28113 Y13137) and the *Saccharomyces pombe* RAD2 gene (GenBank Accession No. X77041). The archaeal genome of *Methanobacterium thermautotrophiculum* has also been sequenced. Although the sequence similarity between FEN-1 and prokaryotic and viral 5'{character pullout}3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (reviewed in Matsui et al., 1999., J. Biol. Chem., 274:18297, Hosfield et al., 1998b, J. Biol. Chem., 273:27154 and Lieber, 1997, BioEssays, 19:233).

A FEN nuclease according to the invention is preferably thermostable. Thermostable FEN nucleases have been isolated and characterized from a variety of thermostable organisms including four archeaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, Proc. Natl. Acad. Sci., USA, 65:168) fragment does not, (Klenow et al., 1971, Eur. J. Biochem., 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 µg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

Nucleic acid polymerases useful in certain embodiments of the invention substantially lack 3' to 5' exonuclease activity and include but are not limited to exo-Pfu DNA polymerase (a mutant form of Pfu DNA polymerase that substantially lacks 3' to 5' exonuclease activity, Cline et al., 1996, Nucleic Acids Research, 24: 3546; U.S. Pat. No. 5,556,772; commercially available from Stratagene, La Jolla, Calif. Catalogue #600163), exo-Tma DNA polymerase (a mutant form of Tma DNA polymerase that substantially lacks 3' to 5' exonuclease activity), exo-Tli DNA polymerase (a mutant form of Tli DNA polymerase that substantially lacks 3' to 5' exonuclease activity New England Biolabs, (Cat #257)), exo-*E. coli* DNA polymerase (a mutant form of *E. coli* DNA polymerase that substantially lacks 3' to 5' exonuclease activity) exo-Klenow fragment of *E. coli* DNA polymerase I (Stratagene, Cat #600069), exo-T7 DNA polymerase (a mutant form of T7 DNA polymerase that substantially lacks 3' to 5' exonuclease activity), exo-KOD DNA polymerase (a mutant form of KOD DNA polymerase that substantially lacks 3' to 5' exonuclease activity), exo-JDF-3 DNA polymerase (a mutant form of JDF-3 DNA polymerase that substantially lacks 3' to 5' exonuclease activity), exo-PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos. 600131, 600132, 600139, Stratagene); U1Tma (N-truncated) *Thermatoga martima* DNA polymerase; Klenow fragment of DNA polymerase I, 9° Nm DNA polymerase (discontinued product from New England Biolabs, Beverly, Mass.), "3'-5' exo reduced" mutant (Southworth et al., 1996, Proc. Natl. Acad. Sci 93:5281) and Sequenase (USB, Cleveland, Ohio). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature.

As used herein, "amplification" refers to any in vitro method for increasing the number of copies of a nucleic acid template sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR; Mullis and Faloona, 1987, Methods Enzymol., 155:335). One PCR reaction may consist of 5 to 100 "cycles" of denaturation and synthesis of a nucleic acid molecule. PCR amplifications with an exo-DNA polymerase inherently will result in generating mutated amplified product.

As used herein, "polymerase chain reaction" or "PCR" refers to an in vitro method for amplifying a specific nucleic acid template sequence. The PCR reaction involves a repetitive series of temperature cycles and is typically performed in a volume of 50-100 µl. The reaction mix comprises dNTPs (each of the four deoxyribonucleotides dATP, dCTP, dGTP, and dTTP), primers, buffers, DNA polymerase, and nucleic acid template. The PCR reaction comprises providing a set of oligonucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of oligonucleotide primers" or "a set of PCR primers" can comprise two, three, four or more primers. In one embodiment, an exo-Pfu DNA polymerase is used to amplify a nucleic acid template in a PCR reaction.

As used herein, the term "PCR primer" refers to a single stranded DNA or RNA molecule that can hybridize to a nucleic acid template and prime enzymatic synthesis of a second nucleic acid strand. A PCR primer useful according to the invention is between 10 to 100 nucleotides in length, preferably 17-50 nucleotides in length and more preferably 17-45 nucleotides in length. In some embodiments, primers of the invention comprise a tag or label that produces a secondary signal which is useful for detection. A tag can be, for example, an additional nucleic acid sequence that can be bound by a secondary sequence to produce a secondary signal.

As used herein, a "PCR reaction buffer" or "reaction buffer" refers to a single buffer composition which allows PCR amplification of a nucleic acid template by a nucleic acid polymerase. The buffer may contain any known chemicals used in a buffer for PCR reactions. Preferably, the buffer contains a buffering composition selected from Tris or Tricine. Preferably, the buffering composition has a pH range of from 7.5 to 9.5. Preferably, the PCR reaction buffer contains $Mg^{2+}$ (e.g., $MgCl_2$ or $MgSO_4$) in the range of 1-10 mM. The buffer according to the invention may also contain $K^+$ (e.g., KCl) in the range of from 0 to 20 mM. In some embodiments, the buffer contains components which enhance PCR yield (e.g., $(NH_4)_2SO_4$ in the range of from 0 to 20 mM). In other embodiments, the buffer contains one or more non-ionic detergents (e.g., Trition X-100, Tween 20, or NP40, in the range of from 0 to 1%). The buffer may also contain BSA (bovine serum albumin) in the range of from 1-100 µg/ml. In a preferred embodiment of the invention, the PCR reaction buffer contains 10 mM KCl, 10 mM $(NH_4)_2SO_4$, 20 mM Tris-Cl (pH 8.8), 2 mM $MgSO_4$, 0.1% Triton X-100, 100 µg/ml BSA. In another preferred embodiment, the buffer contains 10 mM KCl, 10 mM $(NH_4)_2SO_4$, 20 mM Tris-Cl (pH 9.2), 2 mM $MgSO_4$, 0.1% Triton X-100, 100 µg/ml BSA.

As used herein, the term "equivalent amount(s)" refers to components (e.g., dATP, dTTP, dGTP, and dCTP) in the PCR buffer having an equal molar concentration.

As used herein, an "amplified product" refers to the double stranded nucleic acid population at the end of a PCR amplification reaction. The amplified product contains the original nucleic acid template and nucleic acid synthesized by DNA polymerase using the nucleic acid template during the PCR reaction. The amplified product, according to the invention, contains mutations to the original nucleic acid template sequence due to the use of error-prone DNA polymerases in the PCR reaction, e.g., Mutazyme and Taq DNA polymerases.

As used herein, the term "repeating one or more additional subsequent PCR amplification reactions" refers to the subsequent performance of one or more additional PCR amplification reactions comprising incubating a nucleic acid template, at least two PCR primers, an error-prone DNA polymerase under conditions which permit amplification of the nucleic acid template. A subsequent PCR reaction comprises said incubating step using the PCR amplified product of a preceding PCR amplification as template. The amplified product of a preceding PCR amplification reaction may be purified before being used as template for a subsequent PCR reaction by means known in the art, e.g., phenol extraction/ethanol precipitation or column purification. The template for a subsequent PCR amplification reaction may be a portion of or the total amplified product of a preceding PCR amplification. For each subsequent PCR amplification, fresh reagents (e.g., reaction buffer, dNTP, DNA polymerase, primers) are added to the reaction mixture. If a portion of the amplified product of a preceding PCR amplification is used, the volume of a subsequent PCR reaction may be the same as the preceding PCR reaction. If the total amplified product of a preceding PCR reaction is used as template, a subsequent PCR reaction will have larger volume than the preceding PCR reaction.

As used herein, "nucleic acid template" or "target nucleic acid template" refers to a nucleic acid containing an amplified region. The "amplified region," as used herein, is a region of a nucleic acid that is to be either synthesized or amplified by polymerase chain reaction (PCR). For example, an amplified region of a nucleic acid template resides between two sequences to which two PCR primers are complementary.

Description

The inventors have discovered that easily designed but highly effective oligonucleotide probes for the detection of a target nucleic acid sequence, for example in real time PCR analysis, can be formed from a target binding oligonucleotide (first sequence) joined to its complementary sequence (second sequence), optionally through a linker oligonucleotide sequence, to form a hairpin structure comprising stem and, optionally, loop portions. The loop portion contains the optional linker sequence, or just a covalent bond joining the ends of the first and second sequences. The linker sequence, which forms the loop structure, may or may not hybridize to the target sequence. No more than 5 contiguous nucleotides of the optional linker sequence are complementary to the target sequence. In some embodiments comprising a linker, no more than 5 nucleotides anywhere in the linker are complementary to the target sequence when the target sequence is aligned for optimum complementarity to the first sequence. The stem portion optionally contains one or more mismatches between the first and second sequences; the number of mismatches can be used to adjust the melting temperature of the probe. The stem portion may also contain modified nucleotides, for example minor groove binders or LNA, which can alter the affinity of the probe for the target sequence and also can be used to adjust the melting temperature. The probes of the invention also contain an interactive pair of labels, for example a fluorophore/quencher pair, attached at or near the ends of the probe such that a detectable signal, e.g., increased fluorescence emission of the fluorophore, is produced when the probe hybridizes to the target sequence. The probes are termed "Key Probes."

Key Probes have surprisingly strong ability to discriminate between target sequences differing by only a single nucleotide, e.g., mutations, substitutions, alleles, or single nucleotide polymorphisms (SNPs) compared to previously designed oligonucleotide probes. While not limiting the invention with respect to any particular mechanism, it is likely that the inclusion of a second sequence that is at least partially complementary to the first sequence (target binding sequence) renders Key Probes better able to discriminate between single base mismatches than linear probes or probes whose target binding sequence is unaccompanied by a corresponding complementary sequence in the probe. Data obtained with Key Probes show, for example, that an exact match target sequence can be readily detected and quantified when present as only 1% of a DNA sample, while the remaining 99% consisting of a nearly identical target sequence having only a single nucleotide difference produces no detectable signal. Thus, Key Probes have a superior ability to detect and quantify specific mutations, alleles, or polymorphisms in mixtures of nucleic acids containing closely related alternate forms.

Preparation of Primers and Probes

Oligonucleotide probes and primers can be synthesized by any method described below and other methods known in the art. Probes and primers are typically prepared by biological or chemical synthesis, although they can also be prepared by biological purification or degradation, e.g., endonuclease digestion. For short sequences such as probes and primers used in the present invention, chemical synthesis is frequently more economical as compared to biological synthesis. For longer sequences standard replication methods employed in molecular biology can be used such as the use of M13 for single stranded DNA as described by Messing, 1983, Methods Enzymol. 101: 20-78. Chemical methods of polynucleotide or oligonucleotide synthesis include phosphotriester and phosphodiester methods (Narang, et al., Meth. Enzymol. (1979) 68:90) and synthesis on a support (Beaucage, et al., Tetrahedron Letters. (1981) 22:1859-1862) as well as phosphoramidate technique, Caruthers, M. H., et al., Methods in Enzymology (1988)154:287-314 (1988), and others described in "Synthesis and Applications of DNA and RNA," S. A. Narang, editor, Academic Press, New York, 1987, and the references contained therein. Probes of the invention can be formed from a single strand which assumes a secondary structure, typically a hairpin or similar structure, or can be formed from two or more single strands which associate, for example by hybridization of complementary bases, to form a hairpin or similar structure. Label moieties can be attached at any position on any strand, provided that a detectable signal is produced when the target binding sequence of the probe hybridizes to the target sequence.

According to the present invention, the oligonucleotide probe can comprise natural, non-natural nucleotides and analogs. The probe may be a nucleic acid analog or chimera comprising nucleic acid and nucleic acid analog monomer units, such as 2-aminoethylglycine. For example, part or all of the probe may be PNA or a PNA/DNA chimera. Oligonucleotides with minor groove binders (MGBs), locked nucleic acids (LNA) and other modified nucleotides can be used. These oligonucleotides using synthetic nucleotides can have the advantage that the length can be shortened while maintaining a high melting temperature.

Probe Design

The probe of the present invention is ideally less than 150 nucleotides in length, typically less than 100 nucleotides, for example less than 80, 70, 60, or 50 nucleotides in length. Preferably, the probe of the invention is between 10 and 60 nucleotides in length, or between 20 and 40, more preferably between 30 and 60. The desired length of the probe will depend on the intended use of the probe. For example, longer probes may be preferred for hybridization assays in which the target nucleic acid is not amplified prior to detection.

The first sequence of the probe (target binding sequence) is designed such that hybridization to target DNA occurs at the annealing/extension temperature of a hybridization assay or PCR. Therefore, the first sequence of the probe shares homology with the target DNA, whereas the linker, if present, may or may not share homology to the target sequence. If a linker sequence is present, then it should have no more than 5 contiguous nucleotides that are complementary to the target sequence when the target sequence is aligned for optimum complementarity to the first sequence. The region of the target nucleic acid which is at least partially complementary to the first sequence is ideally located within 200 nucleotides downstream of (i.e., to the 3' of) a primer binding site, typically within 150, 125, or 100 nucleotides of a primer binding site, when used in conjunction with PCR. In some embodiments the first sequence is fully complementary over its entire length to the target sequence. In some embodiments the first sequence is fully complementary over its entire length to the second sequence.

The first sequence of the probe is at least 5 nucleotides in length. In preferred embodiments, the first sequence is about 15 to about 60 nucleotides in length. In more preferred embodiments, the first sequence is about 15 to about 30 nucleotides in length. In certain embodiments, the first sequence is about 10 to about 15 nucleotides in length and optionally includes at least one modified nucleotide that increases the $T_m$ of the probe when hybridized to the target.

The second sequence of the probe is at least partially complementary to the first sequence and forms the stem portion of a hairpin structure when the probe is not bound to the target sequence. The second sequence is at least 5 nucleotides in length. Preferably, the second sequence is similar in length to the first sequence. In some embodiments, the first sequence and the second sequence are the same length. The second sequence can be fully complementary to the first sequence. However, in preferred embodiments, there is at least one mismatch between the first sequence and the second sequence. Preferably, there are from about 2 to about 8 mismatches between the first and second sequences, or from about 3 to about 6 mismatches. In certain embodiments, the number of mismatches between the first and second sequences corresponds to from about 10% to about 30% of the length of the first sequence. In some embodiments, the second sequence is identical to the target sequence.

The single-stranded "linker" sequence, if present, intervenes between the two stem-forming regions and can vary in length from 1 to 10 bases, typically 2 to 10 bases, 3 to 10 bases, 4 to 10 bases, 4 bases, or 5 bases. The sequence of the linker can be any sequence; however, no more than 5 contiguous nucleotides of the linker sequence are complementary to the target sequence. In certain embodiments, no more than 4, 3, or 2 contiguous nucleotides of the linker are complementary to the target sequence. In some embodiments, no more than 5, 4, 3, or 2 nucleotides anywhere in the linker are complementary to the target sequence when the target sequence is aligned for optimum complementarity to the first sequence. In some embodiments the loop sequence shares little or no homology with the target DNA sequence or with other regions of the probe. Linker sequences include, but are not limited to, $A_n$ and $T_m$, where n is an integer between 3 and 6.

When the probe is bound to a target nucleic acid, frequently either a 5' flap or a 3' flap is formed. A flap can be formed, for example, by the second sequence which does not hybridize to the target nucleic acid. A flap can also be formed from the combination of the second sequence and a loop sequence, if present. A flap can also be formed by an additional sequence inserted between either the 5' or 3' end of the first sequence and an attached label. If the first sequence is at or near the 5' end of the probe, then a 3' flap can be formed by the second sequence, and the flap optionally may include a loop sequence or portion thereof. If the first sequence is at or near the 3' end of the probe, then a 5' flap can be formed by the second sequence, and the flap optionally may include a loop sequence or portion thereof. When the probe is used in a method including a 5' nuclease, e.g., FEN-1, for the enhancement of a fluorescent signal upon binding to a target nucleic acid, then it is preferred that the probe form a 5' flap when bound to target. In such embodiments employing a 5' nuclease, the second sequence is preferably at or near the 5' end of the probe.

Hairpin structures are subject to denaturation at appropriate conditions, including high temperatures, reduced ionic concentrations, and/or the presence of disruptive chemical agents such as formamide or DMSO. The probes of the present invention preferably form hairpin structure at the annealing/extension temperature, which is typically in the range of 55-65° C. Therefore, probes with a hairpin structure $T_m$ higher than the annealing/extension temperature are preferred. For example, the hairpin structure of the probe can have a $T_m \geqq 55°$ C., $\geqq 60°$ C., $\geqq 62°$ C., or $\geqq 65°$ C. However, $T_m$ generally should not be more than about 15° C. higher than the annealing/extension temperature. In some embodiments the probe has a hairpin structure with $T_m$ in the range from about the annealing/extension temperature to about 5-15° C. above the annealing/extension temperature. The stability and melting temperature of hairpin structures can be estimated, for example, using programs such as mfold (Zuker (1989) Science, 244, 48-52) or Oligo 5.0 (Rychlik & Rhoads (1989) Nucleic Acids Res. 17, 8543-51). The appropriate sequence and length of the stem are chosen such that the hairpin structure of the probe has a melting temperature suitable for the intended annealing/extension temperature (e.g., >60° C. for annealing and extension temperatures of 60° C.).

The $T_m$ of the target binding sequence of the probe, when bound to the target, is in a similar range as the $T_m$ of the hairpin structure, but may be higher or lower than the $T_m$ of the hairpin structure. In some embodiments, the $T_m$ of the hairpin structure is less than the $T_m$ of the target binding sequence bound to the target sequence. However, in other embodiments the $T_m$ of the hairpin structure is greater than the $T_m$ of the target binding sequence bound to the target sequence. For example, in some embodiments the $T_m$ of the hairpin structure is about 3 to 7 degrees C. higher than the $T_m$ of the target binding sequence hybridized to the target sequence.

In preferred embodiments, the $T_m$ of the stem structure formed by the first and second sequences in the absence of target sequence is approximately equal to the annealing temperature of the PCR cycle or hybridization assay, or up to 5-20 degrees C. higher than the annealing temperature. Probes with $T_m$ more than 20 degrees C. higher than the annealing temperature will have difficulty unfolding, or will be unable to unfold during a PCR or hybridization analysis. The $T_m$ of a probe is influenced by the length of the stem portion of the probe and number of mismatches in the stem portion of the probe. In general, each additional mismatch added to the stem region will further reduce $T_m$. Therefore, the number of mismatches can be adjusted to give a desired $T_m$. Mismatches can be positioned at any location within the stem portion of the probe, at either end or in the middle, either grouped or separated. Furthermore, $T_m$ can be modified through the introduction of modified nucleotides, including for example minor groove binders and locked nucleic acids (LNA). Introduction of such modified nucleotides can be used to increase the affinity for the target sequence, to reduce the length of the target binding sequence, or to reduce the number of mismatches required for a desired $T_m$.

Detection Moieties

As used herein, the phrase "interactive pair of labels" as well as the phrase "pair of interactive labels" as well as the phrase "first and second moieties" refer to a pair of molecules which interact physically, optically, or otherwise in such a manner as to permit detection of their proximity by means of a detectable signal. Examples of a "pair of interactive labels" include, but are not limited to, labels suitable for use in fluorescence resonance energy transfer (FRET) (Stryer, L. Ann. Rev. Biochem. 47, 819-846, 1978), scintillation proximity assays (SPA) (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999).

The first and second moieties are "operatively coupled" to the first and second sequences of the probe, respectively. This means that each moiety is coupled to its respective sequence in any manner consistent with its operation, i.e., in any manner consistent with providing a detectable signal upon binding of the first sequence of the probe to the target sequence. For example, the pair of moieties can be either covalently or non-covalently attached to the oligonucleotide probe of the invention. Examples of non-covalent attachment, any of which can be employed to operatively couple the first or second moiety to the probe of the invention, include attachment via hybridization, hydrogen bonds, ionic bonds, hydrophobic interactions, van der Waals interactions, and protein-nucleic acid interactions. Preferred are moieties which are covalently attached at or near the 5' and 3' ends of the probe.

As used herein, references to "fluorescence" or "fluorescent groups" or "fluorophores" include luminescence and luminescent groups, respectively.

An "increase in fluorescence", as used herein, refers to an increase in detectable fluorescence emitted by a fluorophore. An increase in fluorescence may result, for example, when the distance between a fluorophore and a quencher is increased, for example due to elimination of intraprobe hybridization, such that the quenching is reduced. There is an "increase in fluorescence" when the fluorescence emitted by the fluorophore is increased by at least 2 fold, for example 2, 2.5, 3, 4, 5, 6, 7, 8, 10 fold or more.

In certain embodiments, an increase in fluorescence or other detectable signal can be driven not only by hybridization of the probe to its target sequence, but additionally by cleavage of the probe using a nuclease. Cleavage, for example by a 5'-flap endonuclease (e.g., FEN-1) or another nuclease or a polymerase, can be used to further separate the first and second moieties and thus to enhance the signal produced by binding to target. Key Probes intended for use with 5' nucleases have the first sequence (target binding sequence) at or near the 3' end of the probe and the second sequence at or near the 5' end, so as to generate a 5' flap upon hybridization to target. For example, probes for use with 5' nucleases can produce a 5' flap when bound to template if the 5' end of the first sequence is linked, optionally through a linker, to the 3' end of the second sequence. Since the second sequence is not complementary to the target, it forms a flap at the 5' end of the probe. Probes that produce a 3' flap but not a 5' flap when bound to target will not have that flap cleaved off by a 5' nuclease and thus will not experience signal enhancement through the use of a 5' nuclease.

Fluorophores

A pair of interactive labels useful for the invention can comprise a pair of FRET-compatible dyes, or a quencher-dye pair. In one embodiment, the pair comprises a fluorophore-quencher pair.

Oligonucleotide probes of the present invention permit monitoring of amplification reactions by fluorescence. They can be labeled with a fluorophore and quencher in such a manner that the fluorescence emitted by the fluorophore in intact probes is substantially quenched, whereas the fluorescence in cleaved or target hybridized oligonucleotide probes are not quenched, resulting in an increase in overall fluorescence upon probe cleavage or target hybridization. Furthermore, the generation of a fluorescent signal during real-time detection of the amplification products allows accurate quantitation of the initial number of target sequences in a sample.

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3', 6'-dipivaloylfluoresceinyl)-5-carboxylic acid]); 5-Tetrachloro-Fluorescein ([4,7,2',7'-tetrachloro-(3', 6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); DABCYL (4-((4-(dimethylamino) phenyl)azo)benzoic acid) Cy5 (Indodicarbocyanine-5) Cy3 (Indo-dicarbocyanine-3); and BODIPY FL (2,6-dibromo-4, 4-difluoro-5,7-dimethyl-4-bora-3a,4a-diaza-s-indacene-3-proprionic acid), Quasar-670 (Bioreseach Technologies), CalOrange (Bioresearch Technologies), Rox, as well as suitable derivatives thereof.

Quenchers

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more.

The quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993, Proc. Natl. Acad. Sci., 90:2994-2998); Wu et al. (1994, Anal. Biochem., 218:1-13); Pesce et al., editors, Fluorescence Spectroscopy (1971, Marcel Dekker, New York); White et al., Fluorescence Analysis: A Practical Approach (1970, Marcel Dekker, New York); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (1971, Academic Press, New York); Griffiths, Colour and Constitution of Organic Molecules (1976, Academic Press, New York); Bishop, editor, Indicators (1972, Pergamon Press, Oxford); Haugland, Handbook of Fluorescent Probes and Research Chemicals (1992 Molecular Probes, Eugene) Pringsheim, Fluorescence and Phosphorescence (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ullman et al., U.S. Pat. No. 3,996,345; Khanna et al., U.S. Pat. No. 4,351,760, all of which hereby incorporated by reference.

A number of commercially available quenchers are known in the art, and include but are not limited to DABCYL, BHQ-1, BHQ-2, and BHQ-3. The BHQ ("Black Hole Quenchers") quenchers are a new class of dark quenchers that prevent fluorescence until a hybridization event occurs. In addition, these new quenchers have no native fluorescence, virtually eliminating background problems seen with other quenchers. BHQ quenchers can be used to quench almost all reporter dyes and are commercially available, for example, from Biosearch Technologies, Inc (Novato, Calif.).

Attachment of Fluorophore and Quencher

In one embodiment of the invention, the fluorophore or quencher is attached to the 3' nucleotide of the probe. In another embodiment of the invention, the fluorophore or quencher is attached to the 5' nucleotide. In yet another embodiment, the fluorophore or quencher is internally attached to the oligonucleotide probe. In some embodiments, either the fluorophore or quencher is attached to the 5' nucleotide of the probe and the other of said fluorophore or quencher is attached to the 3' nucleotide of the probe. Attachment can be made via direct coupling, or alternatively using a spacer molecule of, for example, from about 1 to about 5 atoms in length.

For the internal attachment of the fluorophore or quencher, linkage can be made using any of the means known in the art. Appropriate linking methodologies for attachment of many dyes to oligonucleotides are described in many references, e.g., Marshall, Histochemical J., 7: 299-303 (1975); Menchen et al., U.S. Pat. No. 5,188,934; Menchen et al., European Patent Application 87310256.0; and Bergot et al., International Application PCT/US90/05565. All are hereby incorporated by reference.

Each member of the fluorophore/quencher pair can be attached anywhere within the probe, preferably at a distance from the other of the pair such that sufficient amount of quenching occurs when the probe is not bound to the target sequence, i.e., when the probe is in the hairpin configuration.

When the oligonucleotide probe is in the hairpin configuration, the moieties of the fluorophore/quencher pair are in a close, quenching relationship. For maximal quenching, the two moieties are ideally close to each other. In some embodiments, the quencher and fluorophore are positioned 30 or fewer nucleotides from each other.

In one embodiment, the invention contemplates the use of a Key Probe that is dual labeled with a fluorophore/quencher pair. When the labeled probe is cleaved by a FEN nuclease (or other nuclease as described herein), the fluorphore and quencher are separated and the remaining fragment will fluoresce. It is contemplated that the placement of the fluorophore and quencher on the downstream probe may be specifically selected to discriminate between invasive and non-invasive cleavage of the portion of the probe that is not complementary to the target. It will be appreciated by one of skill in the art that the following disclosure for positioning of reporter molecules, although described in the context of a fluorophore/quencher pair, is not limited to that specific reporter system. The placement of the reporter molecules described below may also be applied to other reporter systems such as, for example, intercalating dyes, wherein the cleavage of the probe at a specific site would result in quenching of the dye signal. The placement scheme described below may also be used in any reporter system comprising interacting reporter molecules, such as a FRET pair and the like, where the interaction of the molecules may be interrupted by cleavage of the non-complementary portion of the downstream probe.

The Key Probes described herein may be used in target detection assays similar to those described, for example, in U.S. application Ser. No. 11/150,775, filed Jun. 10, 2005, the contents of which are incorporated herein in their entirety. In the context of such an assay, Pfu FEN cleaves the Key Probe oligonucleotide predominantly at a single position relative to the 3' end of an upstream oligonucleotide. For example, if the nucleotides of the Key probe that hybridize to the target are defined to be nucleotides +1 through +X, where +1 is at the end of the 5' portion of the target hybridized region of the probe and +X is at the 3' end of the target hybridized region of the probe (where X equals the number of hybridized residues in the downstream probe). When the upstream oligonucleotide does not overlap with the Key Probe's target hybridized region, but abuts the Key Probe such that there is only a nick between the two oligonucleotides, FEN is expected to cleave between positions +1 and +2 of the target hybridized region of the Key Probe. If the upstream oligonucleotide has a single 3' base that overlaps with the 5' end of the target hybridized region of the Key Probe, and hybridizes with the target at that 3' base position, then cleavage of the probe occurs between positions +2 and +3 of the hybridized region of the Key Probe. Thus, if the 3' end of the upstream oligonucleotide overlaps with the hybridized region of the Key Probe by N nucleotides, and the overlapping region of the 3' end of the upstream oligonucleotide hybridizes to the target in that region, then cleavage occurs between positions +(N+1) and +(N+2) of the target hybridized region of the Key Probe.

Therefore, where the Key Probe has a pre-formed, non-hybridizing 5' end (e.g., 5' flap), cleavage occurs between positions +(N+1) and +(N+2) of the target hybridized region of the probe, provided that the upstream oligonucleotide abuts (and does not overlap) the target hybridized region of the Key Probe. Leaving only a nick between the two oligonucleotides, cleavage will occur between positions +1 and +2 of the hybridized region of the downstream oligonucleotide and release of the probe's 5' flap; the 5' flap will have one nucleotide at its 3' end derived from the 5' end of the hybridized region of the Key Probe. If the upstream oligonucleotide contains one base at its 3' end that overlaps with the target hybridized region of the Key Probe, cleavage will occur between positions +2 and +3 of the probe and release of the probe's 5' flap, now with 2 bases at its 3' end derived from the first 2 target hybridized bases of the probe.

Accordingly, if a reporter group, such as a fluorophore, is attached to base +2 of the target hybridized region of the Key Probe, and a quencher is attached to a base in the 5' flap, then cleavage downstream of position +2 will leave the quencher and the reporter group still attached to the same nucleic acid molecule. However, if cleavage were to occur upstream of position +2 of the probe (i.e., between positions +1 and +2), then the reporter located on base +2 will become separated from the quencher located on the flap. It also follows that if there is to be cleavage upstream of position +2, the upstream probe cannot have an overlap with the target hybridized region of the Key Probe. Thus, invasive cleavage structures in which the upstream oligonucleotide has a 3' portion both complementary to the target and overlapping with the complementary portion of the downstream oligonucleotide, will cause cleavage downstream of position +2 and thus no physical separation of the reporter group located on position +2, and the quencher located in the 5' flap. Cleavage events resulting from invasive cleavage structures will be undetected, whereas cleavage events resulting from non-invasive cleavage structures will be detectable. Thus, placement of the reporter molecule (such as a fluorophore) at position +2 of the target hybridized/complementary portion of the Key Probe permits the discrimination between invasive and non-invasive cleavage. Accordingly, one embodiment of the invention contemplates the placement of the reporter molecule (e.g., fluorophore) at position +2 of the target complementary region of the Key Probe. It is also contemplated that the positioning of the fluorophore/quencher pair may be reversed, such that the flurophore is on the 5' flap and the quencher is located at position +2 of the complementary region of the downstream probe.

The instant invention is also based, in part, on the discovery that placement of a reporter molecule (such as, but not limited to a fluorophore such as FAM (fluorescein)) at position +3 or +9 of the Key Probe should result in no cleavage between positions +3 and +4 or between positions +9 and +10 of the probe, respectively. Therefore, a Key Probe having a fluorophore (e.g., FAM) at position +2 will not be capable of being cleaved between positions +2 and +3, thus an upstream oligonucleotide having a single 3' overlapping base will not be able to cause cleavage of the probe between positions +2 and +3, whereas an upstream oligonucleotide with no overlapping region, just a nick, will cause there to be cleavage between positions +1 and +2, which would separate the reporter group from the quencher present on the 5' flap. Thus, a signal produced by cleavage of a Key Probe with a FAM attached to base +2 of the hybridizing region of the probe will result only from non-invasive cleavage structures, and not from invasive cleavage structures. Moreover, cleavage of a 5' flap from a probe having a fluorophore (e.g., FAM) attached at the +2 position of the complementary region will result in a cleaved flap with one 3' base, or three 3' bases from the 5' end of the complementary region attached to the 3' end of the flap. Such a flap cannot have exactly 2 additional bases attached to its 3' end because the cleavage structure that would result in two 3' bases being left attached to the 5' flap would not be cleaved because of blockage of FEN by the fluorophore on the +2 base of the Key Probe.

Accordingly, the invention contemplates the use of Key Probes having a fluorophore group (such as, but not limited to a FAM group) on base +2 and a quencher upstream (5' prime) of position +1 to generate signals only from non-invasive cleavage structures, and not from invasive cleavage structures.

Amplification of Target Nucleic Acid

In some embodiments, the probe of the invention is used to monitor or detect the presence of a target nucleic acid in a nucleic acid amplification reaction. In such embodiments, the method can be performed, for example, using typical reaction conditions for polymerase chain reaction (PCR). Two temperatures are achieved per cycle: one, a high temperature denaturation step (generally in the range of 90° C.-96° C.), lasting typically between 1 and 30 seconds, and a combined annealing/extension step (typically in the range of 50° C.-65° C., depending on the annealing temperature of the probe and primer and the polymerase chosen for the reaction), usually between 1 and 90 seconds. The reaction mixture, also referred to as the "PCR mixture", contains a nucleic acid, a nucleic acid polymerase as described above, the oligonucleotide probe of the present invention, suitable buffer, and salts. The reaction can be performed in any thermocycler commonly used for PCR. However, preferred are cyclers with quantitative fluorescence measurement capabilities, including Taq Man 7700 AB (Applied Biosystems, Foster City, Calif.), Rotorgene 2000 (Corbett Research, Sydney, Australia), LightCycler (Roche Diagnostics Corp, Indianapolis, Ind.), iCycler (Biorad Laboratories, Hercules, Calif.) and Mx4000 (Stratagene, La Jolla, Calif.).

Use of a labeled probe generally in conjunction with the amplification of a target polynucleotide, for example, by PCR, e.g., is described in many references, such as Innis et al., editors, PCR Protocols (Academic Press, New York, 1989); Sambrook et al., Molecular Cloning, Second Edition (Cold Spring Harbor Laboratory, New York, 1989), all of which are hereby incorporated herein by reference. In preferred embodiments, the binding site of the probe is located between the PCR primers used to amplify the target polynucleotide. Preferably, PCR is carried out using Taq DNA polymerase or an equivalent thermostable DNA polymerase, and the annealing temperature of the PCR is about 5° C.-10° C. below the melting temperature of the oligonucleotide probes employed.

Kits

The invention is intended to provide novel compositions and methods for amplification and/or detection as described herein. The invention herein also contemplates a kit format which comprises a package unit having one or more containers of the subject composition and in some embodiments including containers of various reagents for polynucleotide synthesis, including synthesis in PCR. The kit may also contain one or more of the following items: polymerization enzymes (i.e., one or more nucleic acid polymerase, such as a DNA polymerase, especially a thermostable DNA polymerase), polynucleotide precursors (e.g., nucleoside triphosphates), primers, buffers, instructions, and controls. The kits may include containers of reagents mixed together in suitable proportions for performing the methods in accordance with the invention. Reagent containers preferably contain reagents in unit quantities that obviate measuring steps when performing the subject methods. One kit according to the invention also contains a DNA yield standard for the quantitation of the PCR product yields from a stained gel.

EXAMPLES

The examples below are non-limiting and are merely representative of various aspects and features of the subject invention.

Example 1

Use of Key Probe to Quantify Group B *Streptococcus* DNA

Figure 2A:
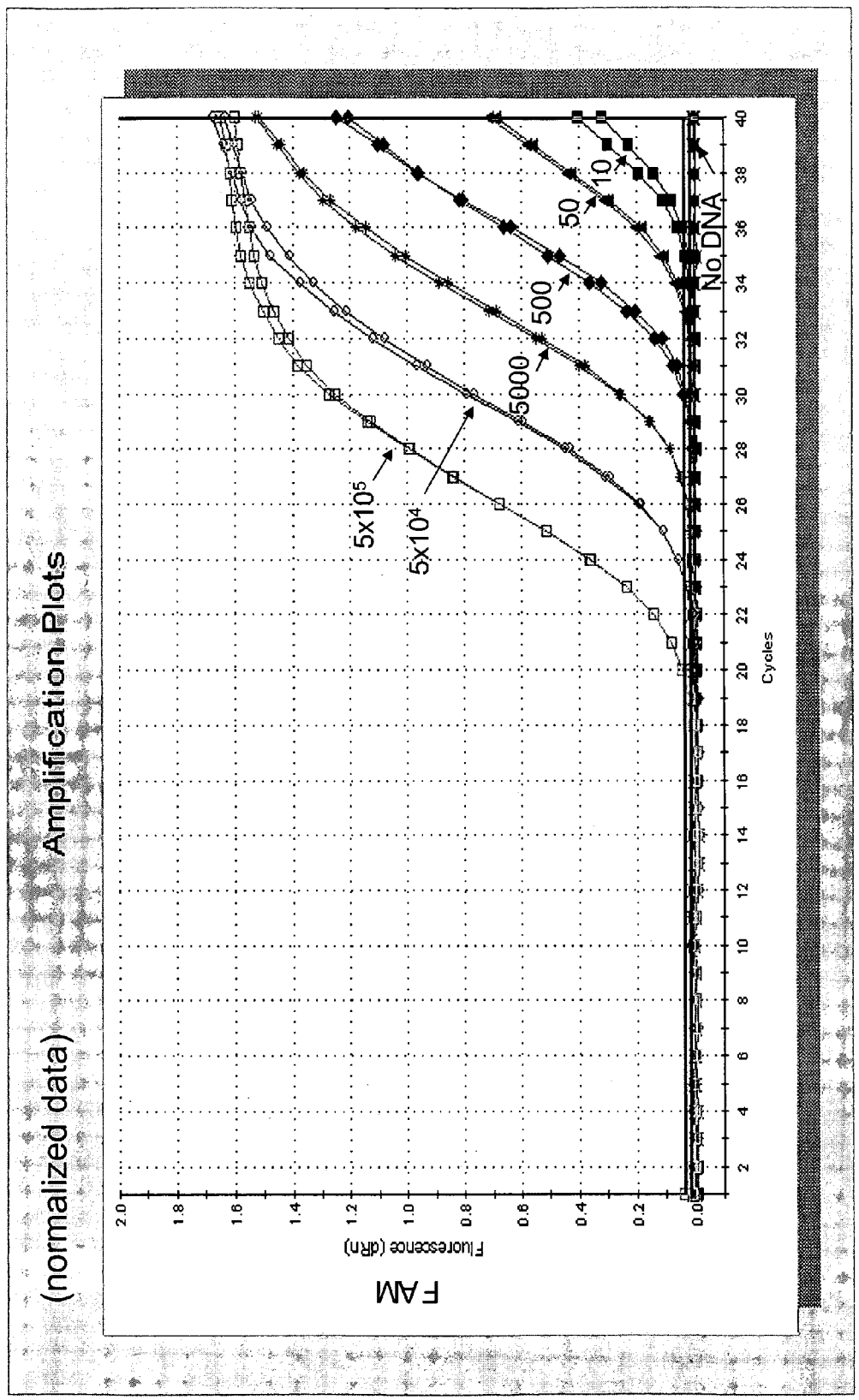
FIG. 2 shows a titration of Group B *Streptococcus* (GBS) DNA using a GBS-specific Key Probe. The probe of FIG. 1 was used to quantify amounts of GBS DNA ranging from 10 to 500,000 copies per assay. Normalized data are presented in FIG. 2A, and raw fluorescence data are presented in FIG. 2B. See Example 1 for details.
Figure 2B:
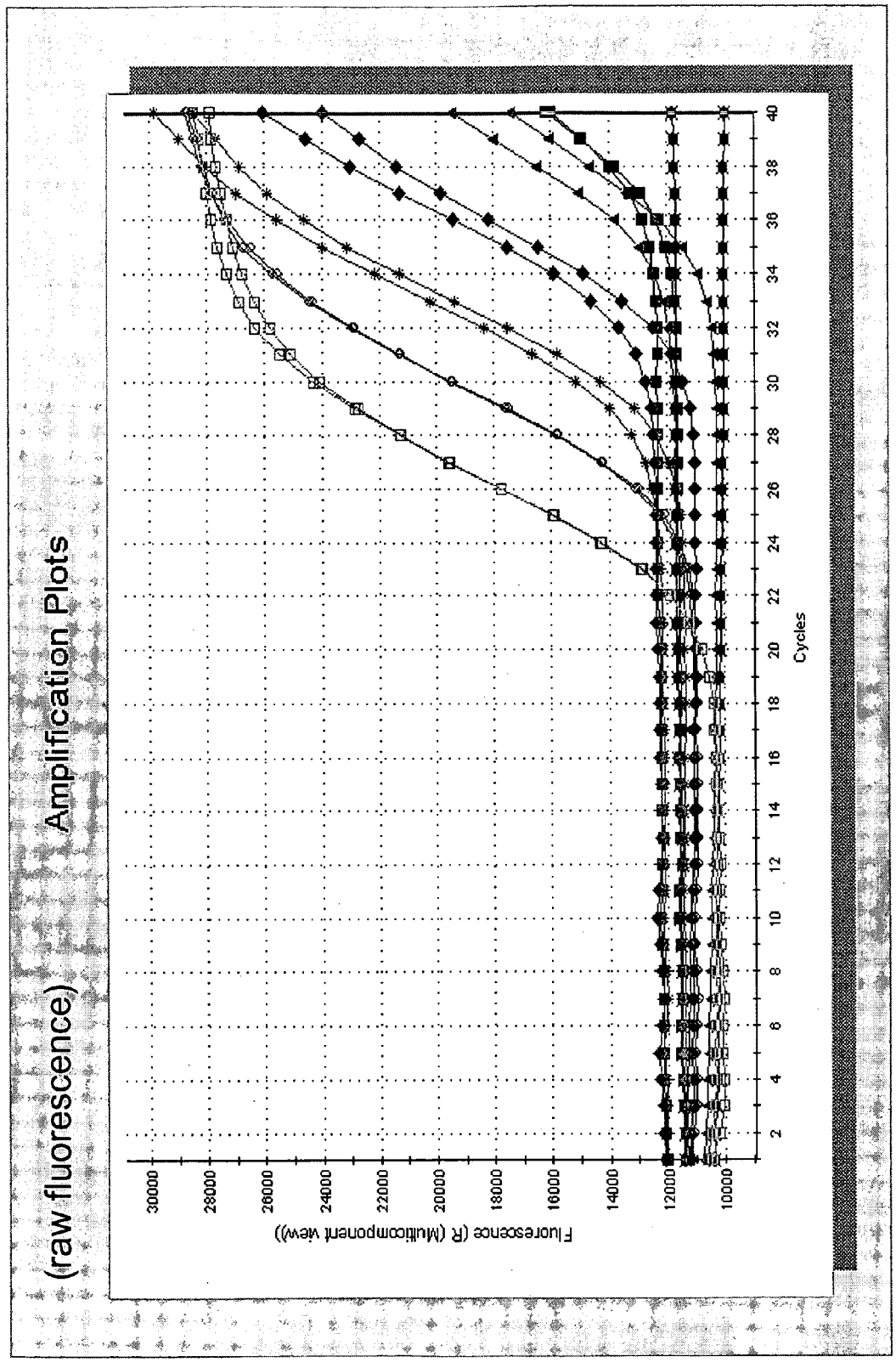

Purified genomic DNA from Streptococcus agalactiae (GBS) ($5\times10^5$, $5\times10^4$, 5000, 500, 50, or 10 copies) was titrated into a FullVelocity™ PCR reaction containing 400 nM GBS-specific primers and 300 nM GBS-specific Key Probe, labeled with 3'-FAM, and quenched with 5'-BHQ-2. The GBS-specific Key Probe is depicted in FIG. 1; its sequence is shown in SEQ ID NO:1. The GBS-specific primers were 5'-acgagtgtcgtgactacgacctta-3' (forward primer, SEQ ID NO:2) and 5'-tctgtcttcgttctaccatcaggc-3' (reverse primer, SEQ ID NO:3). The experiment was conducted on an Mx3000p quantitative PCR instrument (Stratagene) with the following cycling parameters: 2 min at 95° C., followed by 40 cycles of 1 sec at 95° C., 18 sec at 60° C. Data were normalized by inclusion of 30 nM ROX reference dye in each reaction and are expressed as dRn (change in FAM fluorescence, normalized to the reference dye) with respect to cycle number. Normalized data are shown in FIG. 2A. Raw fluorescence data presented in FIG. 2B show the background signals of the KEY probe (between 10000 and 12000 raw fluorescence units). A no-template sample lacking GBS DNA was included as a negative control. Each reaction was performed in duplicate. Full Velocity™ QPCR Master Mix is Stratagene Catalog No. 600561 and is described further in U.S. Pat. Nos. 6,528,254 and 6,548,250 (each incorporated herein by reference in its entirety).

Figure 3:
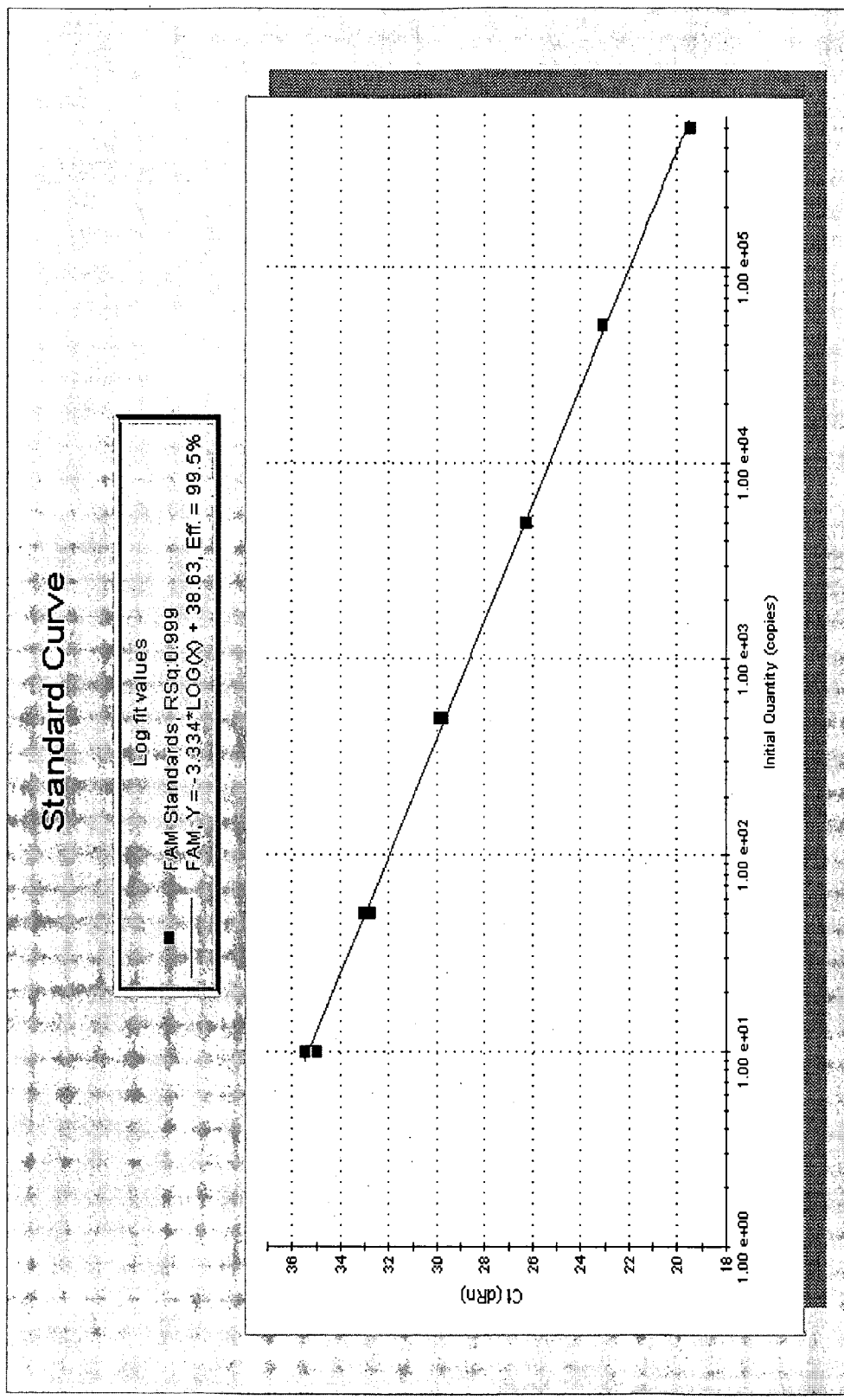
FIG. 3 is a standard curve prepared from the data presented in FIG. 2A.

A standard curve prepared from the data is shown as FIG. 3. Data are presented as $C_t$ vs. input DNA copy number. $C_t$ (threshold cycle) is the cycle number at which fluorescence signal exceeds a selected threshold level; in this case the threshold level (solid line near the bottom of FIG. 2A) was determined by the Mx3000p software. Data points are fit to a line by linear regression analysis. The $R^2$ value for linear fit of these data is 0.999, and the calculated efficiency of amplification (generated from the slope of the best-fit line) is 99.5%. These data suggest nearly perfect doubling of target DNA with each cycle, and nearly perfect concentration-dependence of PCR signal with respect to initial GBS DNA copy number.

Example 2

Allelic Discrimination Using a Key Probe Pair with 3' Flap

Figure 4B:
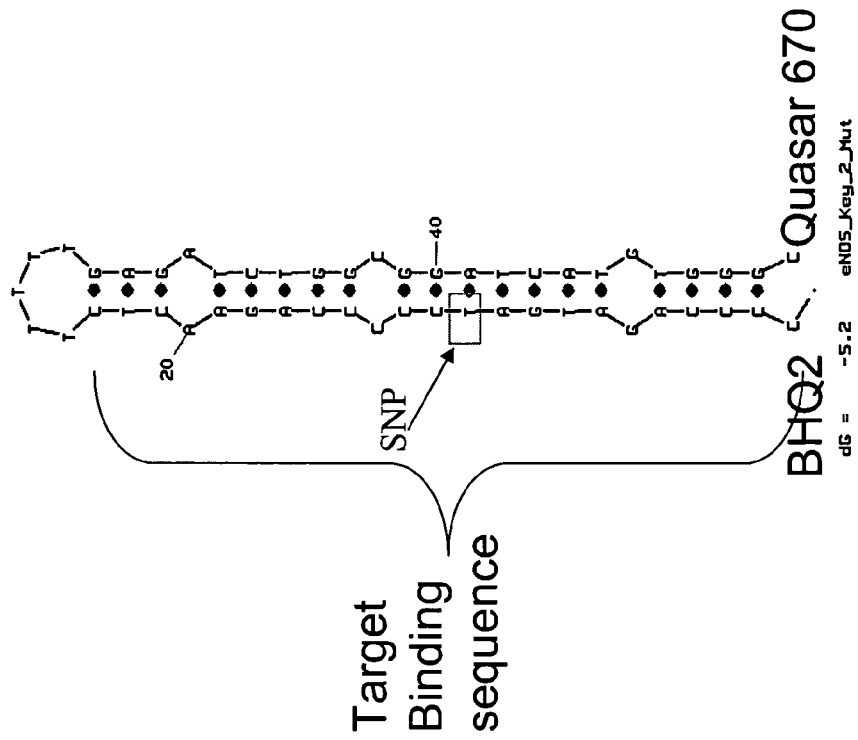
FIG. 4 illustrates the sequence and secondary structure of a matched pair of Key Probes which are able to discriminate between two alleles at a single nucleotide polymorphism (SNP) of DNA encoding eNOS (endothelial nitric oxide synthase) and which generate a 3' flap. One probe is specific for wild-type (FIG. 4A) and the other for a mutant form (SNP) (FIG. 4B). The probe position recognizing the SNP is indicated by a rectangle. The probes in FIGS. 4A and 4B both have the target binding sequence (sequence 1) at the 5' end and thus generate a 3' flap when hybridized to a nucleic acid containing the target sequence.
Figure 4A:
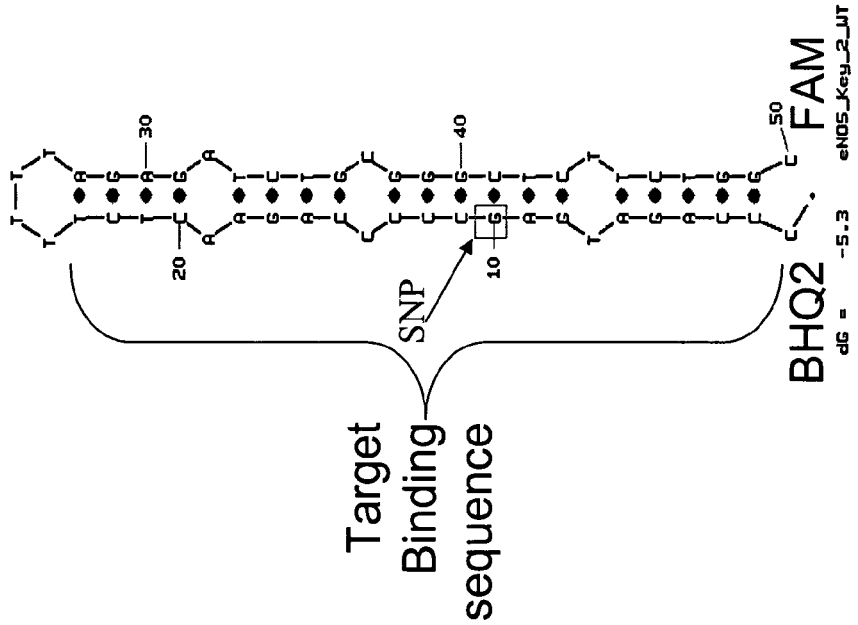

PCR reactions were conducted using a pair of eNOS (endothelial nitric oxide synthase) Key Probes. The wild type probe (3'FAM-labeled, with 5' BHQ-2 quencher) is shown in FIG. 4A, and its sequence is shown in SEQ ID NO:4). The matching mutant probe (3' Quasar-670-labeled, with 5' BHQ-2 quencher) is shown in FIG. 4B, and its sequence is shown in SEQ ID NO:5). Templates were purified PCR products obtained using either wild-type or mutant DNA. The eNOS wild type template had the following sequence: 5'-cccaggaaacggtcgcttcgacgtgct-gccctgctgctgcaggccccagatga[g]cccccag aactcttccttctgc-cccccgagctggtccttgaggtgccctggag-3' (SEQ ID NO:6). The eNOS mutant template had the following sequence: 5'-cccag-gaaacggtcgcttcgacgtgctgccctgctgctgcaggccccagatga[t] cccccag aactcttccttctgcccccgagctggtccttgaggtgccctggag-3' (SEQ ID NO:7). Both templates were obtained using the following primer pair: 5'-cccaggaaacggtcgcttcg-3'(forward primer, SEQ ID NO:8) and 5'-ctccagggggcacctcaagg-3'(reverse primer, SEQ ID NO:9).

Figure 5A:
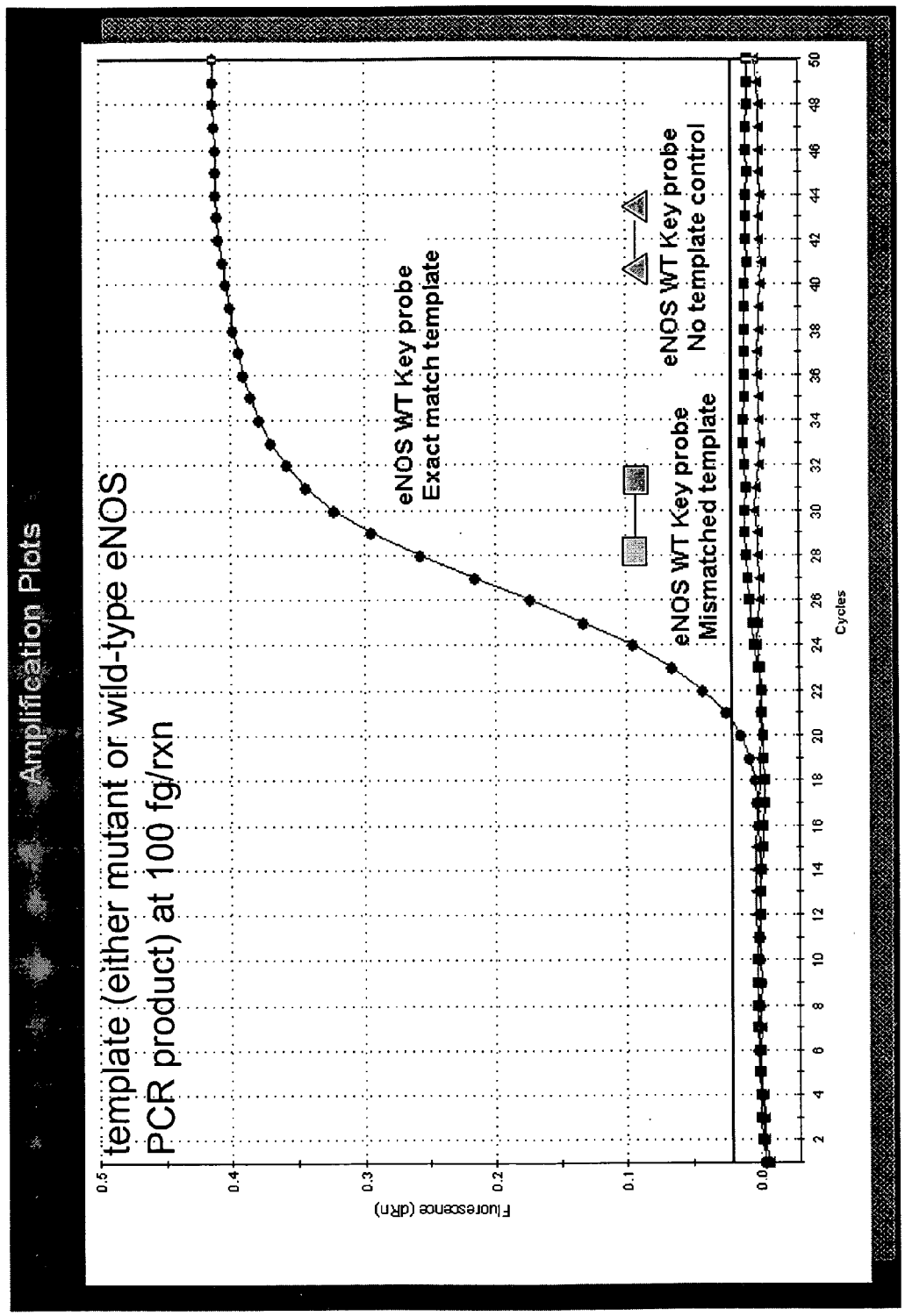
In FIG. 5A results are shown for template containing exact match wild-type eNOS DNA (circles), mutant (i.e., mismatched) eNOS DNA (squares), and control reactions performed without eNOS DNA template (triangles).

A FullVelocity™ PCR reaction was conducted using the eNOS wild-type Key Probe with matching wild-type template (G-allele, circles), mismatched mutant template (T-allele, squares), or no DNA as a negative control (triangles). Templates were purified PCR products from either wild-type or mutant DNA and were present at 100 fg per reaction. The forward PCR primer (eNOS-k-Fwd) was present at 500 nM, the reverse PCR primer (eNOS-k-Rev) was present at 100 nM and the eNOS wild type Key Probe was present at 400 nM. Data were normalized by inclusion of 30 nM ROX reference dye in each reaction. The experiment was conducted on an Mx3000p real-time PCR instrument with the following cycling parameters: 2 min at 95° C., 50 cycles of 95° C. 10 s, 60° C. 30 s. Data are expressed as dRn (change in FAM fluorescence, normalized to the reference dye) with respect to cycle number. The results are depicted in FIG. 5A.

Figure 5B:
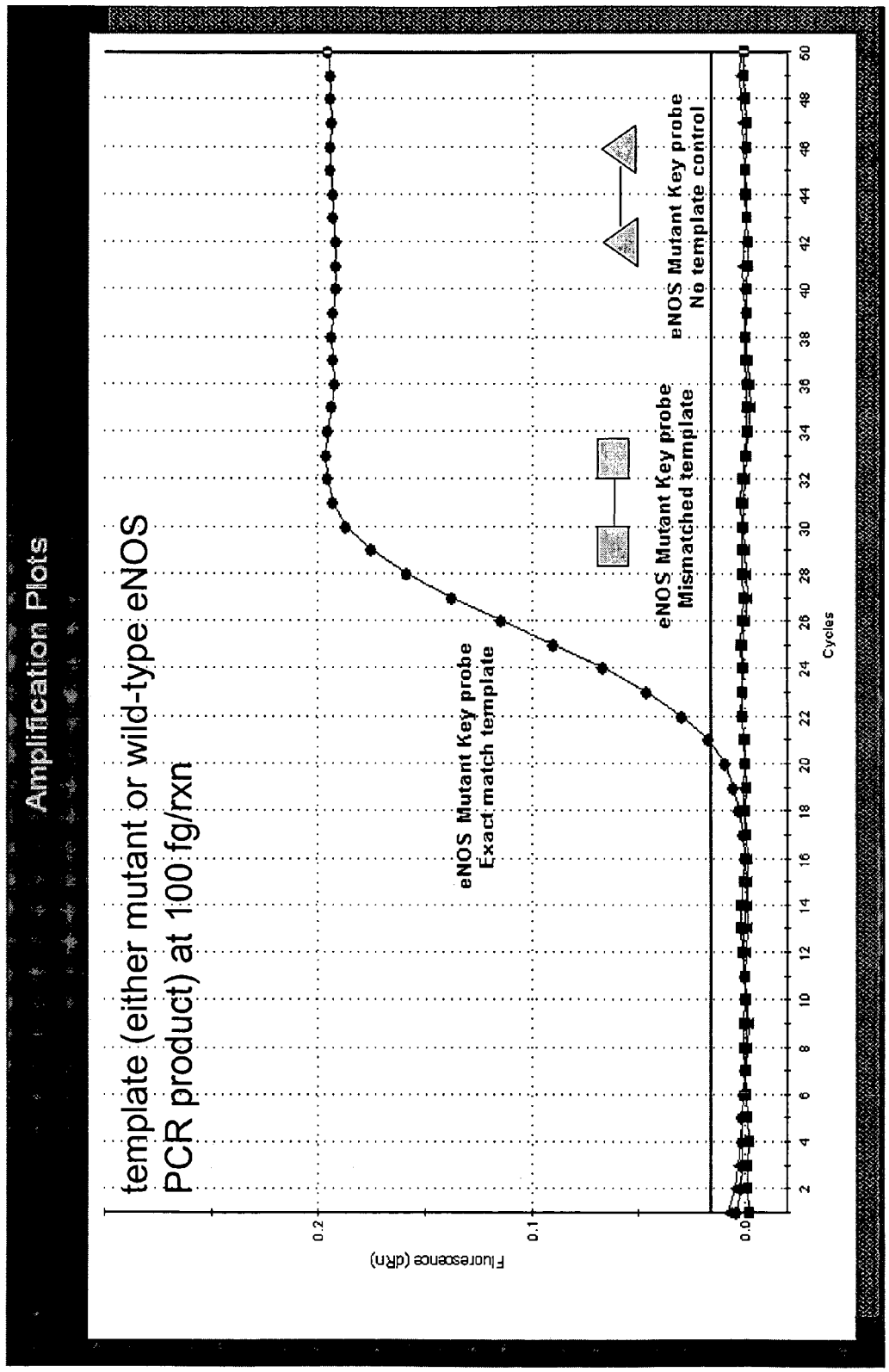
In FIG. 5B results are shown for template containing exact match mutant eNOS DNA (circles), wild-type (i.e., mismatched) eNOS DNA (squares), and control reactions performed without eNOS DNA template (triangles). See Example 2 for details.

A Full Velocity™ PCR reaction was conducted using the eNOS mutant Key Probe with matching mutant template (T-allele, circles), mismatched wild-type template (G-allele, squares), or no DNA as a negative control (triangles). The forward PCR primer (eNOS-k-Fwd) was present at 500 nM, the reverse PCR primer (eNOS-k-Rev) was present at 100 nM and the eNOS mutant KEY probe was present at 400 nM. Cycle parameters and data normalization were same as for the wild type Key Probe reaction described above. Note that Quasar-670 is a direct replacement for CY5, and is thus reported in the CY5 channel. The results are depicted in FIG. 5B.

Figure 6A:
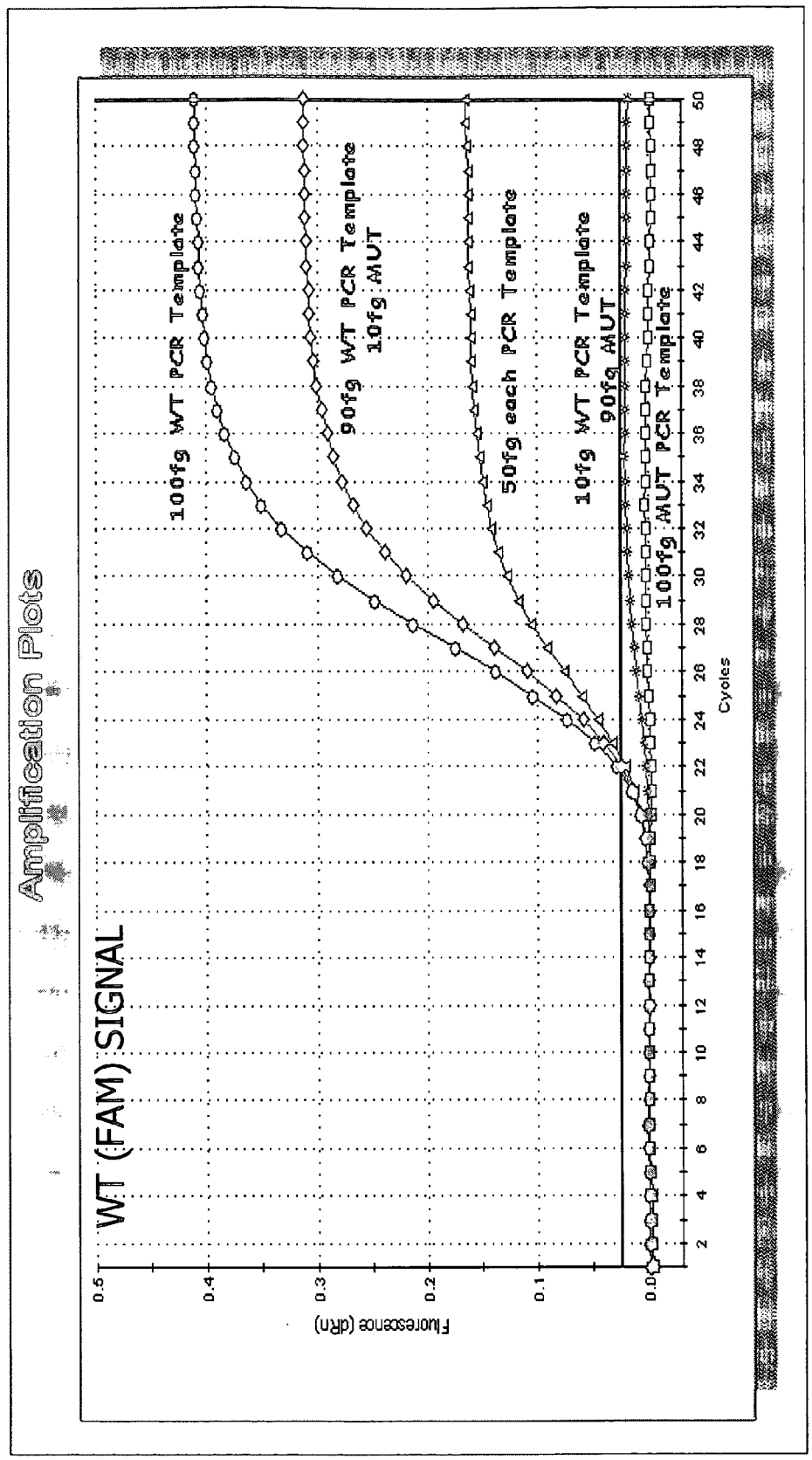
In FIG. 6A, the signal of the wild-type specific Key Probe is presented.

A FullVelocity™ PCR reaction was conducted using both wild-type (FAM-labeled) and mutant (Quasar 670-labeled) KEY probes in the same reaction. The signal generated from the wild-type probe (FAM channel) is shown in FIG. 6A. Total template concentration was 100 fg/reaction, but the ratio of wild-type (G-allele) to mutant (T-allele) PCR product template was varied as follows: 100 fg of either wild-type or mutant template alone, 50 fg of each template, or 90 fg of one and 10 fg of the other template. The forward PCR primer (eNOS-k-Fwd) was present at 500 nM, the reverse PCR primer (eNOS-k-Rev) was present at 100 nM and each eNOS KEY probe was present at 400 nM. Cycle parameters and data normalization were same as described above. Data are expressed as dRn (change in FAM fluorescence, normalized to the reference dye) with respect to cycle number.

Figure 6B:
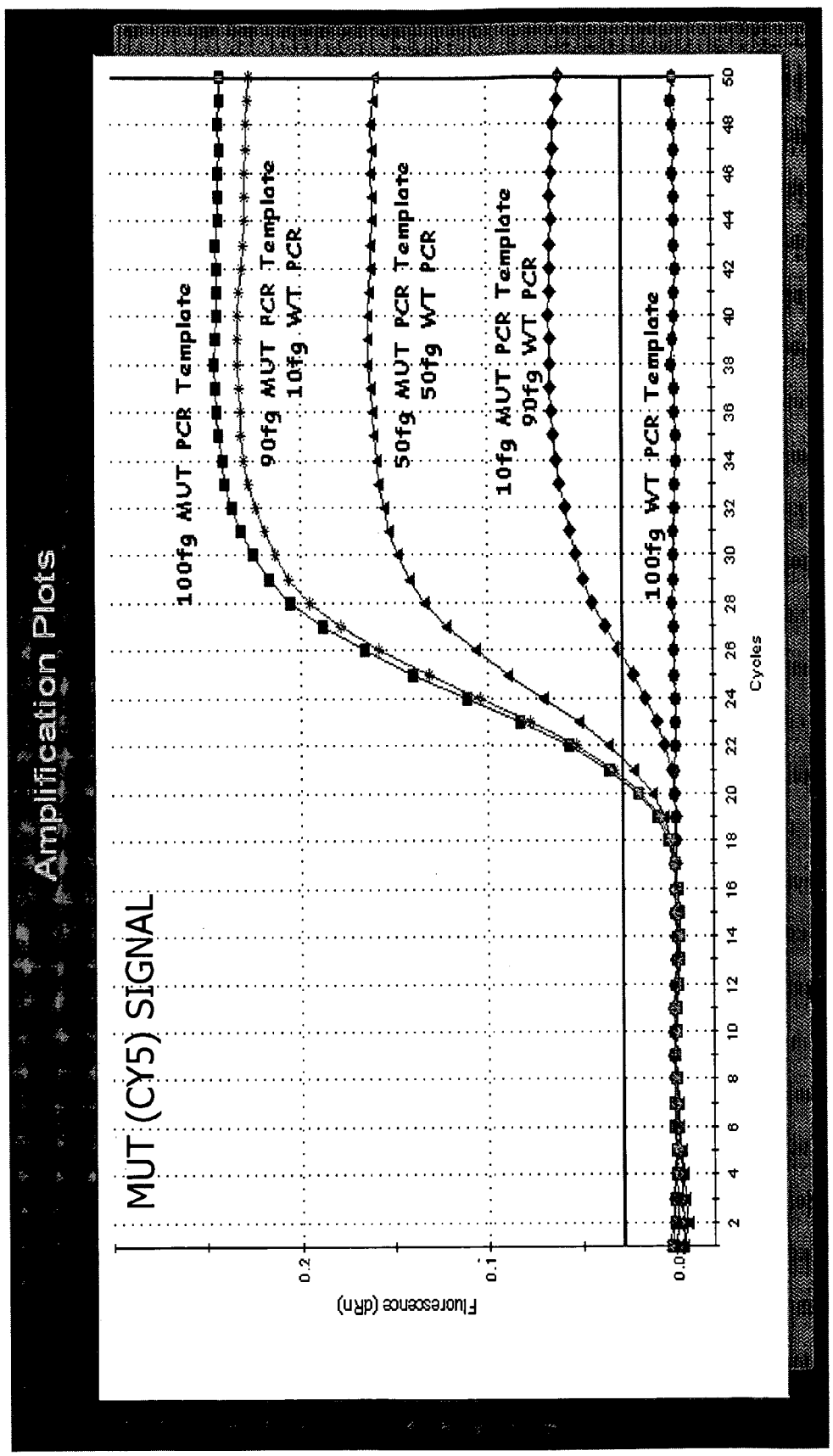
In FIG. 6B, the signal of the mutant-specific Key Probe is presented. See Example 2 for details.

A FullVelocity™ PCR reaction was conducted using both wild-type (FAM-labeled) and mutant (Quasar 670-labeled) KEY probes in the same reaction. The signal generated from the mutant probe (Quasar 670 fluorescence shown in CY5 channel) is shown in FIG. 6B. Total template concentration was 100 fg/reaction, but the ratio of wild-type (G-allele) to mutant (T-allele) PCR product template was varied as follows: 100 fg of either wild-type or mutant template alone, 50 fg of each template, or 90 fg of one and 10 fg of the other template. The forward PCR primer (eNOS-k-Fwd) was present at 500 nM, the reverse PCR primer (eNOS-k-Rev) was present at 100 nM and each eNOS KEY probe was present at 400 nM. Cycle parameters and data normalization were same as described above. Data are expressed as dRn (change in Quasar 670 fluorescence, normalized to the reference dye) with respect to cycle number.

Example 3

Allelic Discrimination Using a Key Probe Pair With 5' Flap

Figure 7B:
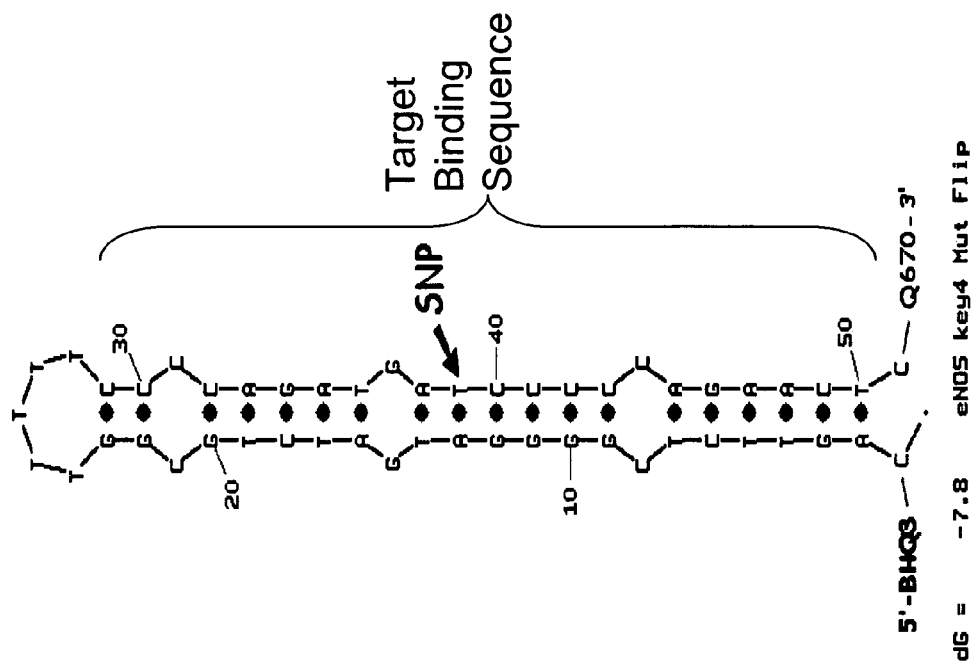
FIG. 7 illustrates the sequence and secondary structure of a matched pair of Key Probes which are able to discriminate between two alleles at a single nucleotide polymorphism (SNP) of DNA encoding eNOS (endothelial nitric oxide synthase) and which generate a 5' flap when bound to DNA encoding eNOS. One probe is specific for wild-type (FIG. 7A) and the other for a mutant form (SNP) (FIG. 7B). The probe position recognizing the SNP is indicated by an arrow. The probes in FIGS. 7A and 7B both have the target binding sequence (sequence 1) at the 3' end and thus generate a 5' flap when hybridized to a nucleic acid containing the eNOS target sequence.
Figure 7A:
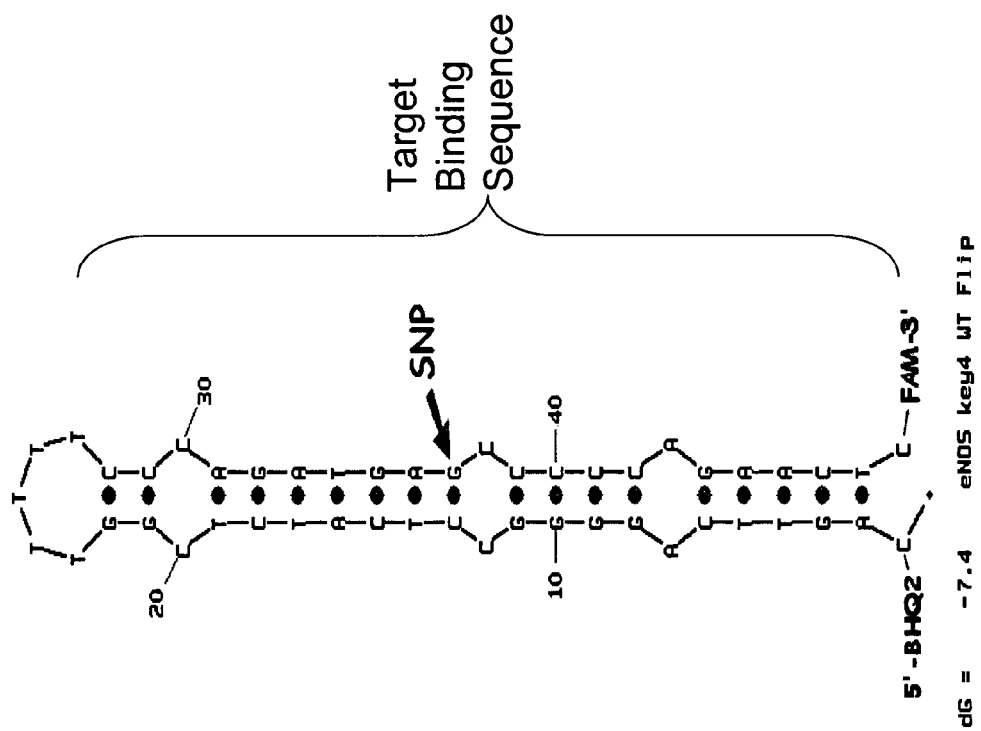

PCR reactions were conducted using the pair of eNOS Key Probes shown in FIGS. 7A and 7B. The sequence of the wild type probe is shown in SEQ ID NO:10 and that of the matching mutant probe is shown in SEQ ID NO:11. The wild type probe was labeled with 3' FAM and 5' BHQ-2 quencher. The mutant probe was labeled with 3' Quasar-670 and 5' BHQ-2 quencher. Templates were purified PCR products obtained using either wild-type or mutant DNA, and were the same templates as described in Example 2.

Figure 8:
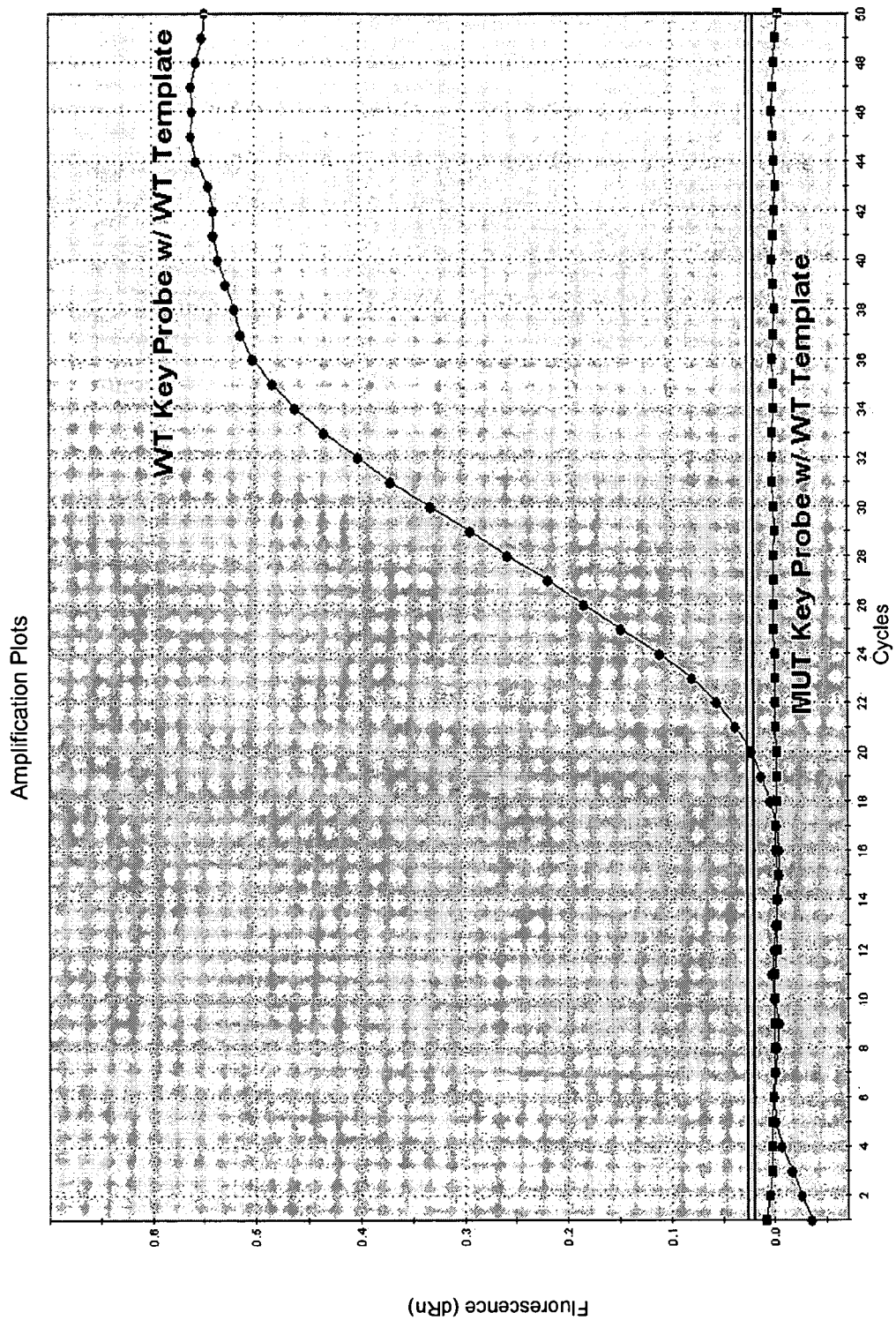
FIG. 8 depicts the results of an allelic discrimination assay using the wild-type eNOS-specific Key Probe of FIG. 7A (circles) and the mutant eNOS-specific Key Probe of FIG. 7B (squares) to detect a target nucleic acid sequence having the wild type sequence. See Example 3 for details.
Figure 9:
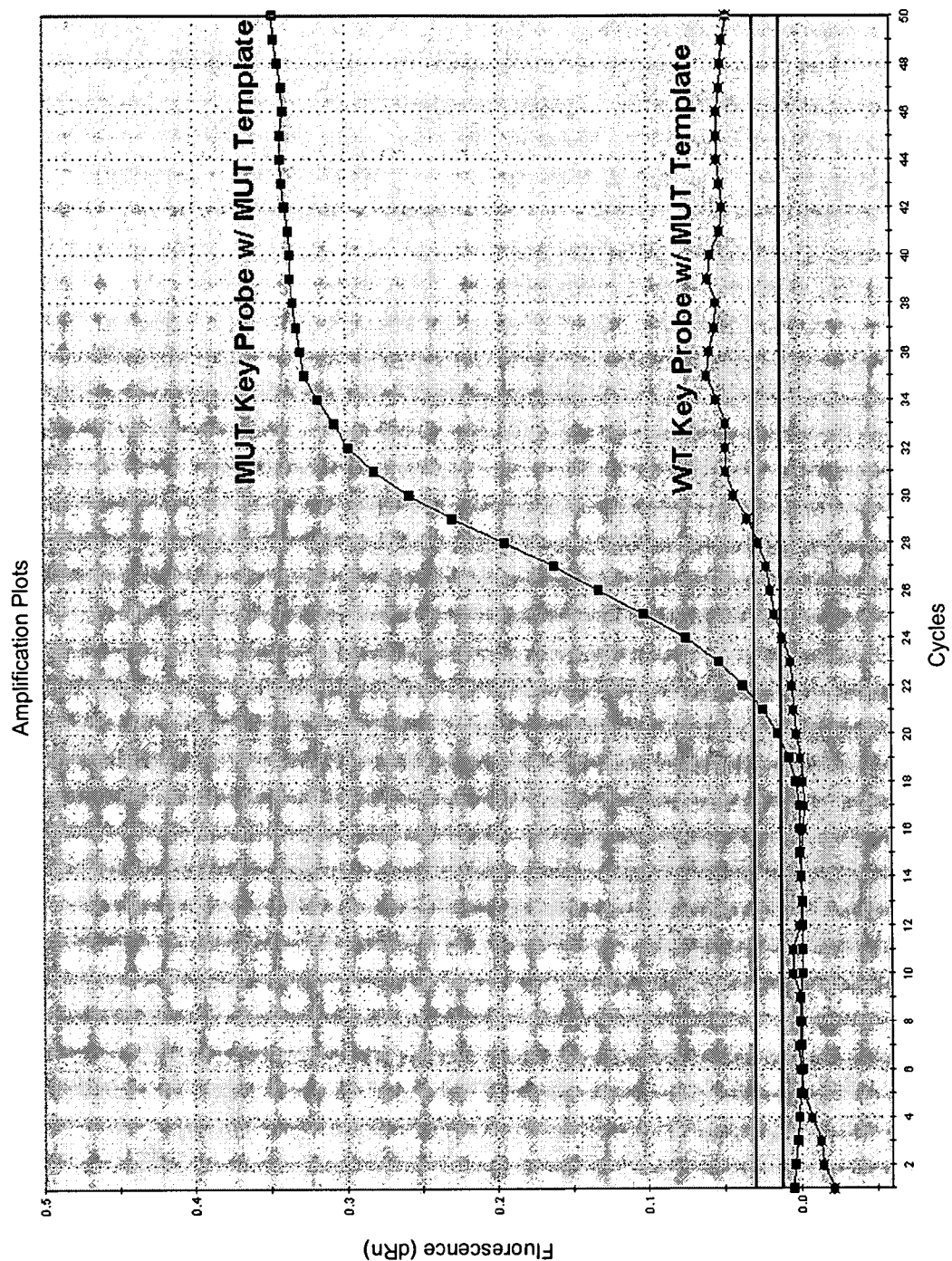
FIG. 9 depicts the results of an allelic discrimination assay using the wild-type eNOS-specific Key Probe of FIG. 7A (*) and the mutant eNOS-specific Key Probe of FIG. 7B (squares) to detect a target nucleic acid sequence having the mutant eNOS sequence. See Example 3 for details.

A FullVelocity™ PCR reaction was conducted using both eNOS wild-type Key Probes of FIGS. 7A and 7B with either wild type template (results shown in FIG. 8) or with mutant template (results shown in FIG. 9). Templates were purified PCR products from either wild-type or mutant DNA and were present at 100 fg per reaction. The forward PCR primer (same as in Example 2) was present at 400 nM, the reverse PCR primer (same as in Example 2) was present at 400 nM and the eNOS wild type Key Probes were present at 400 nM each. Data were normalized by inclusion of 30 nM ROX reference dye in each reaction. The experiment was conducted on an Mx300p real-time PCR instrument with the following cycling parameters: 2 min at 95° C., 50 cycles of 95° C. 10s, 60° C. 30s. Data are expressed as dRn (change in FAM or BHQ fluorescence, normalized to the reference dye) with respect to cycle number.

Example 4

This Example shows variations of the Key Probe which may be used to determine the optimal placement of fluorophore/quencher pairs to achieve the best signal following specific non-invasive cleavage (assays for such target detection and cleavage detection are taught, for example in U.S. application Ser. No. 11/150,775, filed Jun. 10, 2005, the contents of which are incorporated herein in their entirety). FIGS. 10-13 show an example of the method of the invention which combines a Key Probe with the specific positioning of a fluorophore (e.g., FAM) at position +2 of the 5' end of the target complementary region of the Key Probe.

FIG. 10 shows an example of a target amplicon sequence (SEQ ID NO:12). The portion of the target sequence that is complementary to the Key Probe is shown in bold, and the portion of the target sequence that is complementary to the upstream 3' blocked probe is shown in italics. FIGS. 11 and 12 show various embodiments of key probes which may be used according to the invention. FIG. 11A depicts a control probe; that is, the fluorophore and quencher moieties are placed at the 3' and 5' ends, respectively, of the probe sequence (SEQ ID NO:13), and the ability of the non-target complementary portion of this probe to be cleaved should not be dependent on the positioning of the fluorophore (unlike the embodiments described above, where the fluorophore is specifically placed at position +2). FIG. 11B shows an example of a Key Probe based on the same nucleotide sequence (SEQ ID NO:13) as the probe in FIG. 11A, in which the FAM molecule is placed at position +2 of the 5' end of the complementary region of the Key Probe. This probe also shows the positioning of the quencher BHQ2 at the −8 position (that is, 8 residues 5' of the 5' end of the complementary region). In this example, the quencher cannot be placed at the −7 without changing the −7 position to a thymine (T), and it is expected that the standard Key Probe structure may be adversely affected by such a conversion. FIGS. 12A and B show a Key Probe having the FAM moiety at position +2, and the BHQ2 quencher located at positions −3 and −1 respectively. The probe sequence is the same as that in FIGS. 11A and 11B (SEQ ID NO:13). It is expected that the specific positioning of the quencher moiety relative to the fluorophore at position +2 may have an effect on the efficiency and sufficiency of quenching and/or fluorescence following cleavage of the non-target complementary region of the Key Probe.

FIG. 13 shows examples of the upstream 3' blocked oligonucleotide probes having 0-3 nucleotides of overlap at the 3' end with the 5' end of the complementary region of the Key Probes. The sequence with 0 nt of overlap is SEQ ID NO:14; the sequence with 1 nt of overlap is SEQ ID NO:15; the sequence with 2 nt of overlap is SEQ ID NO:16; and the sequence with 3 nt of overlap is SEQ ID NO:17. The synthetic amplicon strand is SEQ ID NO:18. It is expected that the Key Probe having FAM at the +2 position will only be cleaved to produce a fluorescent signal where there is no overlap of the blocked oligonucleotide probe and 5' end of the the downstream Key Probe.

The invention claimed is:

1. A method of detecting a target nucleic acid sequence, comprising the steps of (1) incubating the target sequence with a probe capable of binding to a target nucleic acid sequence, said probe comprising (a) a first sequence which is at least partially complementary to a target sequence and has a stem portion and a loop portion, wherein the loop portion does not hybridize to the target sequence: (b) a second sequence which is at least partially complementary to the stem portion of the first sequence: (c) a first moiety operatively coupled to the first sequence: and (d) a second moiety operatively coupled to the second sequence: wherein the 3' end of the first sequence is linked to the 5' end of the second sequence: wherein the stem portion of the first sequence and the second sequence are capable of hybridizing to each other when the probe is not hybridized to the target sequence: and wherein hybridization of the probe to the target sequence causes either the first moiety or the second moiety to produce a detectable signal: and (2) detecting a signal from the first or second moiety, wherein the step of incubating is performed in the presence of a nuclease.

2. The method of claim 1 wherein the nuclease is a flap endonuclease.

3. The method of claim 2 wherein a detectable signal is produced if the flap endonuclease performs an invasive cleavage.

4. The method of claim 2 wherein a detectable signal is produced if the flap endonuclease performs a non-invasive cleavage.

5. A method of detecting a target nucleic acid sequence, comprising the steps of (1) amplifying the target sequence using a polymerase chain reaction in the presence of a probe capable of binding to the target sequence, said probe comprising (a) a first sequence which is at least partially complementary to the target sequence and which consists of a stem portion and a loop portion, wherein the loop portion does not hybridize to the target sequence; (b) a second sequence which is shorter than the first sequence and at least partially complementary to the stem portion of the first sequence; and (c) first and second moieties; wherein the 3' end of the first sequence is linked to the 5' end of the second sequence; wherein the first sequence and the second sequence are capable of hybridizing to each other when the probe is not hybridized to the target sequence; and wherein hybridization of the probe to the target sequence causes the first or second moiety to produce a detectable signal; and (2) detecting a signal from the first or second moiety.

6. The method of claim 5 wherein the step of incubating amplifying is performed in the presence of a nuclease.

7. The method of claim 6 wherein the nuclease is a flap endonuclease.

8. The method of claim 7 wherein a detectable signal is produced if the flap endonuclease produces an invasive cleavage.

9. The method of claim 7 wherein a detectable signal is produced if the flap endonuclease produces a non-invasive cleavage.

* * * * *

SEQUENCE LISTING

<160> NUMBER OF SEQ ID NOS: 18

<210> SEQ ID NO 1
<211> LENGTH: 57
<212> TYPE: DNA
<213> ORGANISM: Artificial sequence
<220> FEATURE:
<223> OTHER INFORMATION: Oligonucleotide probe

<400> SEQUENCE: 1
acctacaaca gaaccatcgc aaccctaaaa aagggtagcg atcgttctct tgtagga    57

<210> SEQ ID NO 2
<211> LENGTH: 24
<212> TYPE: DNA
<213> ORGANISM: Artificial sequence
<220> FEATURE:
<223> OTHER INFORMATION: PCR primer

<400> SEQUENCE: 2
acgagtgtcg tgactacgac ctta    24

<210> SEQ ID NO 3
<211> LENGTH: 24
<212> TYPE: DNA
<213> ORGANISM: Artificial sequence
<220> FEATURE:
<223> OTHER INFORMATION: PCR primer

<400> SEQUENCE: 3
tctgtcttcg ttctaccatc aggc    24

<210> SEQ ID NO 4
<211> LENGTH: 50
<212> TYPE: DNA
<213> ORGANISM: Artificial sequence
<220> FEATURE:
<223> OTHER INFORMATION: Oligonucleotide probe

<400> SEQUENCE: 4
cccagatgag cccccagaac tcttttttaga gatctgcggg ctcttctggc    50

<210> SEQ ID NO 5
<211> LENGTH: 50
<212> TYPE: DNA
<213> ORGANISM: Artificial sequence
<220> FEATURE:
<223> OTHER INFORMATION: Oligonucleotide probe

<400> SEQUENCE: 5
cccagatgat cccccagaac tcttttttaga gatctgcggg ctcttctggc    50

<210> SEQ ID NO 6
<211> LENGTH: 109
<212> TYPE: DNA
<213> ORGANISM: Artificial sequence
<220> FEATURE:
<223> OTHER INFORMATION: DNA template

<400> SEQUENCE: 6
cccaggaaac ggtcgcttcg acgtgctgcc cctgctgctg caggcccag atgagccccc    60 agaactcttc cttctgcccc ccgagctggt ccttgaggtg cccctggag    109

<210> SEQ ID NO 7
<211> LENGTH: 109
<212> TYPE: DNA
<213> ORGANISM: Artificial sequence
<220> FEATURE:
<223> OTHER INFORMATION: DNA template

<400> SEQUENCE: 7

```
cccaggaaac ggtcgcttcg acgtgctgcc cctgctgctg caggccccag atgatccccc    60
agaactcttc cttctgcccc ccgagctggt ccttgaggtg cccctggag               109
```

<210> SEQ ID NO 8
<211> LENGTH: 20
<212> TYPE: DNA
<213> ORGANISM: Artificial sequence
<220> FEATURE:
<223> OTHER INFORMATION: PCR primer

<400> SEQUENCE: 8

```
cccaggaaac ggtcgcttcg                                                20
```

<210> SEQ ID NO 9
<211> LENGTH: 19
<212> TYPE: DNA
<213> ORGANISM: Artificial sequence
<220> FEATURE:
<223> OTHER INFORMATION: PCR primer

<400> SEQUENCE: 9

```
ctccaggggc acctcaagg                                                 19
```

<210> SEQ ID NO 10
<211> LENGTH: 49
<212> TYPE: DNA
<213> ORGANISM: Artificial sequence
<220> FEATURE:
<223> OTHER INFORMATION: Oligonucleotide probe

<400> SEQUENCE: 10

```
cagttcaggg gcctcatctc ggttttcccc agatgagccc ccagaactc                49
```

<210> SEQ ID NO 11
<211> LENGTH: 49
<212> TYPE: DNA
<213> ORGANISM: Artificial sequence
<220> FEATURE:
<223> OTHER INFORMATION: Oligonucleotide probe

<400> SEQUENCE: 11

```
cagttcaggg gcctcatctc ggttttcccc agatgatccc ccagaactc                49
```

<210> SEQ ID NO 12
<211> LENGTH: 238
<212> TYPE: DNA
<213> ORGANISM: Artificial sequence
<220> FEATURE:
<223> OTHER INFORMATION: DNA template

<400> SEQUENCE: 12

```
cctgaacacg cacctgctga aatgtatgac ataatgaaga cttgctggga tgcagatccc    60
ctaaaaagac caacattcaa gcaaattgtt cagctaattg agaagcagat ttcagagagc   120
accaatcata tttactccaa cttagcaaac tgcagcccca accgacagaa gcccgtggta   180
gaccattctg tgcggatcaa ttctgtcggc agcaccgctt cctcctccca gcctctgc    238
```

```
<210> SEQ ID NO 13
<211> LENGTH: 55
<212> TYPE: DNA
<213> ORGANISM: Artificial sequence
<220> FEATURE:
<223> OTHER INFORMATION: Oligonucleotide probe

<400> SEQUENCE: 13
gccaagcgag agatgcgcgt cgtagttttt ctaccacggg cttctgtcgg ttggg      55

<210> SEQ ID NO 14
<211> LENGTH: 28
<212> TYPE: DNA
<213> ORGANISM: Artificial sequence
<220> FEATURE:
<223> OTHER INFORMATION: Oligonucleotide probe

<400> SEQUENCE: 14
ccgacagaat tgatccgcac agaatggt                                    28

<210> SEQ ID NO 15
<211> LENGTH: 29
<212> TYPE: DNA
<213> ORGANISM: Artificial sequence
<220> FEATURE:
<223> OTHER INFORMATION: Oligonucleotide probe

<400> SEQUENCE: 15
ccgacagaat tgatccgcac agaatggtc                                   29

<210> SEQ ID NO 16
<211> LENGTH: 30
<212> TYPE: DNA
<213> ORGANISM: Artificial sequence
<220> FEATURE:
<223> OTHER INFORMATION: Oligonucleotide probe

<400> SEQUENCE: 16
ccgacagaat tgatccgcac agaatggtct                                  30

<210> SEQ ID NO 17
<211> LENGTH: 31
<212> TYPE: DNA
<213> ORGANISM: Artificial sequence
<220> FEATURE:
<223> OTHER INFORMATION: Oligonucleotide probe

<400> SEQUENCE: 17
ccgacagaat tgatccgcac agaatggtct a                                31

<210> SEQ ID NO 18
<211> LENGTH: 53
<212> TYPE: DNA
<213> ORGANISM: Artificial sequence
<220> FEATURE:
<223> OTHER INFORMATION: DNA template

<400> SEQUENCE: 18
cccaaccgac agaagcccgt ggtagaccat tctgtgcgga tcaattctgt cgg        53
```